United States Patent
Denny et al.

(10) Patent No.: US 7,776,924 B2
(45) Date of Patent: Aug. 17, 2010

(54) NITROANILINE-BASED ALKYLATING AGENTS AND THEIR USE AS PRODRUGS

(75) Inventors: William Alexander Denny, Auckland (NZ); Graham J. Atwell, Auckland (NZ); Shangjin Yang, Auckland (NZ); William Robert Wilson, Waiuku (NZ); Adam Vorn Patterson, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 185 days.

(21) Appl. No.: 10/529,772

(22) PCT Filed: Oct. 8, 2003

(86) PCT No.: PCT/NZ03/00225

§ 371 (c)(1),
(2), (4) Date: Jun. 2, 2005

(87) PCT Pub. No.: WO2004/033415

PCT Pub. Date: Apr. 22, 2004

(65) Prior Publication Data

US 2005/0256191 A1 Nov. 17, 2005

(30) Foreign Application Priority Data

Oct. 8, 2002 (NZ) ........................ 521851

(51) Int. Cl.
*A61K 31/135* (2006.01)
*C07C 237/28* (2006.01)
(52) U.S. Cl. ...................... 514/646; 564/166
(58) Field of Classification Search .............. 564/166; 514/646
See application file for complete search history.

(56) References Cited

FOREIGN PATENT DOCUMENTS

WO WO 93/11099 6/1993

OTHER PUBLICATIONS

Friedlos et al. "Mustard Prodrugs for Activation by *Escherichia coli* Nitroreductase in Gene-Directed Enzyme Prodrug Therapy" J. Med. Chem., 1997, vol. 40, pp. 1270-1275.*
Patani et al. "Bioisosterism: A Rational Approach in Drug Design" Chem. Rev., 1996, vol. 96, pp. 3147-3176.*
Helsby, N.A., et al; "Chemical Research in Toxicology"; vol. 16(4); pp. 469-478 (2003); STN File CA, Abstract No. 138:331354.
Friedlos, F., et al; "Mustard Prodrugs for Activation by *Escherichia coli* Nitroreductase in Gene-Directed Enzyme Prodrug Therapy"; *J. Med. Chem.*; vol. 40; pp. 1270-1275 (1997).
Marais, R., et al; "Gene-directed Enzyme Prodrug Therapy with a Mustard Prodrug/Carboxypeptidase G2 Combination[1]"; *Cancer Research*, vol. 56, No. 20; pp. 4732-4742 (1996) SP001012313.
Helsby, N.S., et al; "Effect of Nitroreduction on the Alkylating Reactivity and Cytotoxicity of the 2,4-Dinitrobenzamide-5-aziridine CB 1954 and the Corresponding Nitrogen Mustard SN 23862: Distinct Mechanisms of Bioreductive Activation"; *Chemical Research in Toxicology*; vol. 16, No. 4; pp. 469-478 (2003) XP002397204.

* cited by examiner

*Primary Examiner*—Joseph R Kosack
(74) *Attorney, Agent, or Firm*—Nixon & Vanderhye

(57) ABSTRACT

Nitroaniline-based unsymmetrical mustards of the general formula (I) are provided, together with methods of preparation and methods for their use as prodrugs for gene-dependent enzyme prodrug therapy (GDEPT) and cell ablation therapy in conjunction with nitroreductase enzymes as hypoxia selective cytotoxins and as anticancer agents.

10 Claims, No Drawings

NITROANILINE-BASED ALKYLATING AGENTS AND THEIR USE AS PRODRUGS

This application is the U.S. National Phase of International Application PCT/NZ2003/000225, filed Oct. 8, 2003, which designated the U.S. PCT/NZ2003/000225 claims priority to New Zealand Application No. NZ 521851 filed Oct. 8, 2002. The entire content of these applications are incorporated herein by reference.

The present invention relates to the preparation of nitroaniline-based unsymmetrical mustards, and their use as prodrugs for GDEPT (gene-dependent enzyme-prodrug therapy) and cell ablation therapy in conjunction with nitroreductase enzymes, as hypoxia-selective cytotoxins, and as anticancer agents.

BACKGROUND TO THE INVENTION

The use of tumour-selective prodrugs (relatively inactive compounds that can be selectively converted to more active compounds in vivo) is a valuable concept in cancer therapy.

For example a prodrug may be converted into an antitumour agent under the influence of an enzyme that is linkable to a monoclonal antibody that will bind to a tumour associated antigen. The combination of such a prodrug with such an enzyme monoclonal/antibody conjugate represents a very powerful clinical agent. This approach to cancer therapy, often referred to as "antibody directed enzyme/prodrug therapy" (ADEPT), is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al., *Proc. Natl. Acad. Sci. USA* (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, *Annu. Rev. Biochem,* 1993, 62; 191. The term "GDEPT" (gene-directed enzyme prodrug therapy) is used to include both viral and non-viral delivery systems.

4-Nitroaromatic compounds are reduced by both mammalian and bacterial flavoprotein enzymes, which effect stepwise addition of up to six electrons. The major enzymic metabolite is usually the 4-electron species (hydroxylamine).

The present invention relates to novel nitroaniline-based unsymmetrical mustards having cytotoxic activity, to methods of preparing the novel compounds, and to the use of these compounds as prodrugs for GDEPT and for cell ablation therapy in conjunction with nitroreductase enzymes (particularly the nitro reductases encoded by the nfsB gene of *E. coli* or by *Clostridia* species), as hypoxia-selective cytotoxins, and as anticancer agents.

Both dinitrobenzamide aziridines (e.g., 1) [Knox et al., *Cancer Met. Rev.,* 1993, 12, 195] and nitro- and dinitrobenzamide mustards (e.g., 2-4) [Friedlos et al., *J. Med. Chem.,* 1997, 40, 1270] have been reported as substrates for the aerobic *E. coli* nitroreductase (NTR), and as specific prodrugs for GDEPT in conjunction with NTR.

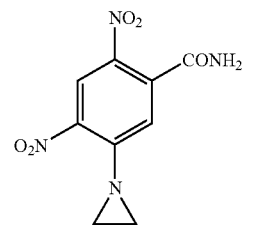

1

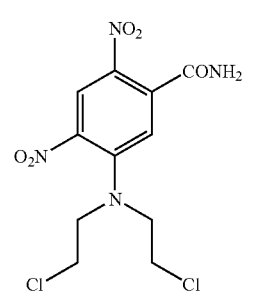

2

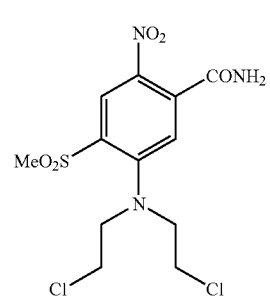

3

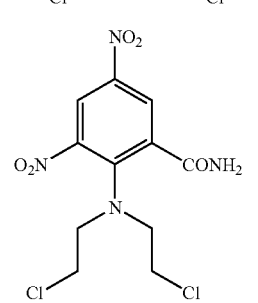

4

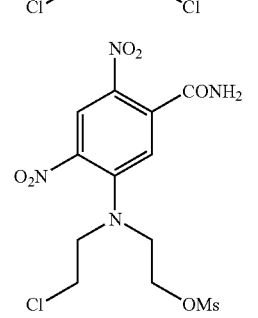

5

Unsymmetrical (chloro-mesylate) mustards have been reported [e.g., Marais et al., *Cancer Res.* 1996, 56, 4735], including the dinitro analogue 5 [Friedlos et al., *J. Med. Chem.* 1997, 40, 1270], which was described as not sufficiently potent for a full biological evaluation to be conducted.

It is therefore an object of the invention to provide a series of unsymmetrical mustards, methods for preparing the unsymmetrical mustards that are suitable for use as prodrugs for GDEPT (gene-dependent enzyme-prodrug therapy) and cell ablation therapy in conjunction with nitroreductase enzymes, as hypoxia-selective cytotoxins, and as anticancer agents or to at least provide the public with a useful alternative.

SUMMARY OF THE INVENTION

In a first aspect, the present invention provides a nitroaniline-based unsymmetrical mustard represented by the general formula (I);

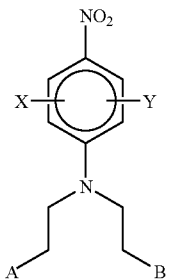
(I)

wherein X represents one of the groups $NO_2$, CN, or $SO_2R^1$, where $R^1$ represents a $C_{1-6}$-lower alkyl optionally substituted with one or more hydroxy and/or one or more amino groups and wherein when $R^1$ represents a tertiary amine the N-oxide derivative of the tertiary amine is further included;

Y represents one of the groups $OR^2$, $NHCOR^2$, $CONR^2CO_2R^3$, $CONR^2$morpholide, $CONHR^2$, $CONR^2R^3$, $CONHOR^2$, $CONHSO_2R^2$, $SO_2NH_2$, $SO_2NHR^2$ or $SO_2NR^2R^3$ wherein each $R^2$ and $R^3$ independently represent a H, $C_{1-6}$-lower alkyl optionally substituted with one or more hydroxy and/or one or more amino groups; and A and B each independently represent halogen, $OSO_2R^4$, $OSO_2NH_2$, $OSO_2NHR^4$ or $OSO_2NR^4R^5$, wherein each $R^4$ and $R^5$ independently represent a $C_{1-6}$-lower alkyl optionally substituted with one or more hydroxy and/or one or more amino groups and wherein when each $R^4$ and $R^5$ independently represents a tertiary amine the N-oxide derivative of the tertiary amine is further included;

and pharmaceutically acceptable derivatives and salts thereof;

with the proviso (i) that A≠B and (ii) that

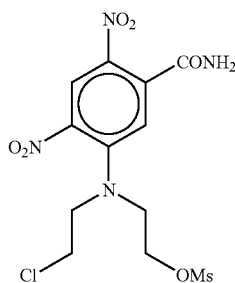

is excluded.

In a preferred embodiment the nitroaniline-based unsymmetrical mustard is selected from a compound represented by one of formulae (IIa-IIc)

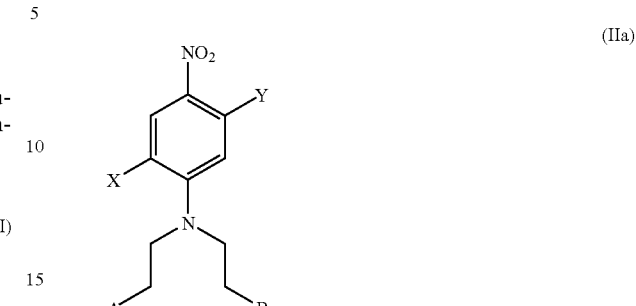
(IIa)

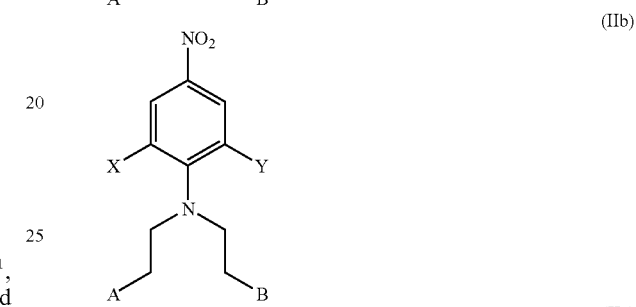
(IIb)

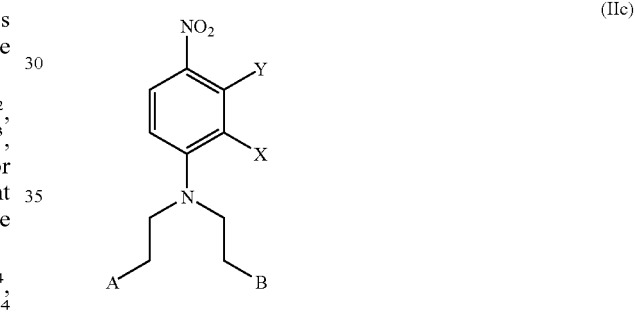
(IIc)

wherein X, Y, A and B are as defined above for a compound of Formula (I); and pharmaceutically acceptable derivatives and salts thereof;

with the proviso (i) that A≠B and (iii) that

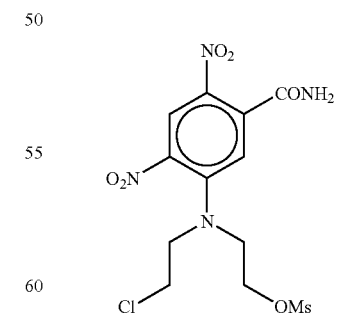

is excluded as a compound of Formula (IIa).

In a more preferred embodiment the nitroaniline-based unsymmetrical mustard is selected from a compound represented by one of formulae (IIIa-IIIc)

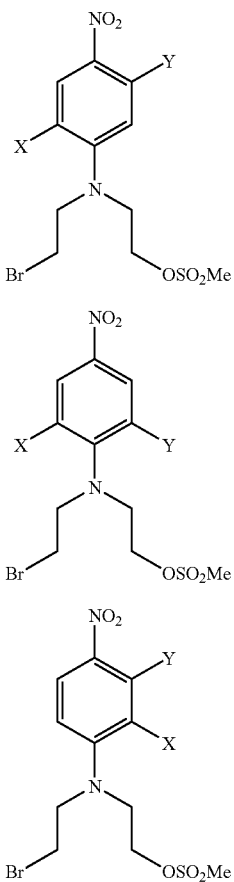

(IIIa)

(IIIb)

(IIIc)

wherein X, Y, are as defined above for a compound of Formula (I); and pharmaceutically acceptable derivatives and salts thereof.

In a second aspect of the invention there is provided a method of preparing a nitroaniline-based unsymmetrical mustard represented by the general formula (I);

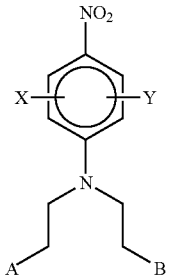

(I)

wherein X represents one of the groups $NO_2$, CN, or $SO_2R^1$, where $R^1$ represents a $C_{1-6}$-lower alkyl optionally substituted with one or more hydroxy and/or one or more amino groups and wherein when $R^1$ represents a tertiary amine the N-oxide derivative of the tertiary amine is further included;

Y represents one of the groups $OR^2$, $NHCOR^2$, $CONR^2CO_2R^3$, $CONR^2$morpholide, $CONHR^2$, $CONR^2R^3$, $CONHOR^2$, $CONHSO_2R^2$, $SO_2NH_2$, $SO_2NHR^2$ or $SO_2NR^2R^3$ wherein each $R^2$ and $R^3$ independently represent a H, $C_{1-6}$-lower alkyl optionally substituted with one or more hydroxy and/or one or more amino groups; and A and B each independently represent halogen, $OSO_2R^4$, $OSO_2NH_2$, $OSO_2NHR^4$ or $OSO_2NR^4R^5$, wherein each $R^4$ and $R^5$ independently represent a $C_{1-6}$-lower alkyl optionally substituted with one or more hydroxy and/or one or more amino groups and wherein when each $R^4$ and $R^5$ independently represents a tertiary amine the N-oxide derivative of the tertiary amine is further included;

and pharmaceutically acceptable derivatives and salts thereof;

with the proviso (i) that A≠B the method including the step of (i) reacting a compound of

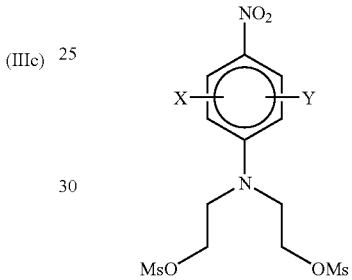

with an amount of an alkali metal halide in a polar solvent to give an unsymmetrical halo-mesylate compound.

In a preferred embodiment the method of preparing a nitroaniline-based unsymmetrical mustard represented by the general formula represented by one of formulae (IIa-IIc)

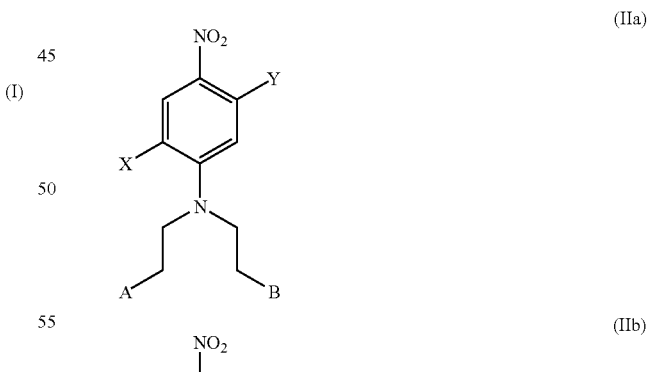

(IIa)

(IIb)

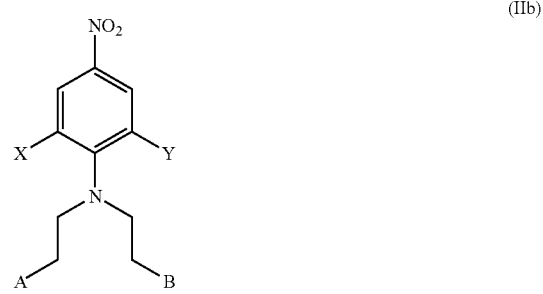

(IIc)

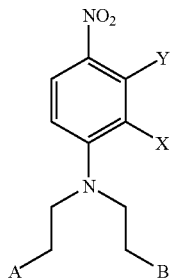

wherein X, Y, A and B are as defined above for a compound of Formula (I); and pharmaceutically acceptable derivatives and salts thereof;

with the proviso (i) that A≠B and the method including the step of (i) reacting a compound of

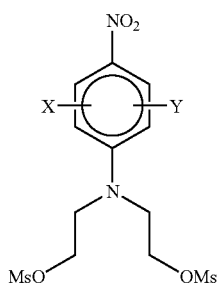

with an amount of an alkali metal halide or mesylate halide in a polar solvent to give a unsymmetrical halo-mesylate compound.

In a more preferred embodiment the method of preparing a nitroaniline-based unsymmetrical mustard represented by one of formulae (IIIa-IIIc)

(IIIa)

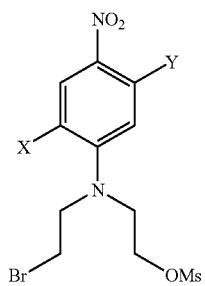

(IIIb)

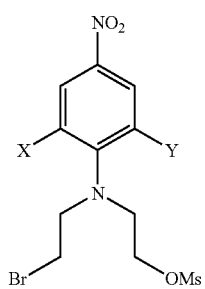

(IIIc)

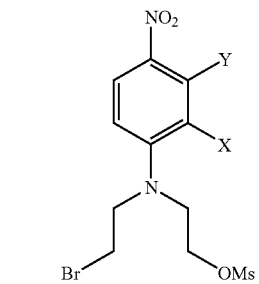

wherein X, Y, are as defined above for a compound of Formula (I); and pharmaceutically acceptable derivatives and salts thereof; the method including the step of (ii) reacting a compound of

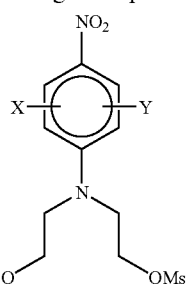

with an amount of LiBr in a polar solvent to give a bromo mesylate of one of formulae (IIIa-IIIc).

It is preferred in the methods defined above that the polar solvent is selected from acetonitrile, dimethylformamide, ethyl acetate, triethylamine, acetone and mixtures thereof.

It is preferred in the methods defined above that the alkali metal halide is selected from one or more of the following; LiCl, LiBr, NaI and NaBr.

In a third aspect there is provided a compound of formula (I) obtained by any one of the preparative methods defined above.

In a fourth aspect, the present invention provides a method for the use as prodrugs suitable for GDEPT (gene-dependent enzyme-prodrug therapy) in conjunction with at least one nitroreductase enzyme, as hypoxia-selective cytotoxins, including the step of administering a compound of Formula I as defined above or a compound of Formulae Ia-Ic, IIa-IIc and IIIa-c as defined above or a mixture thereof in a "therapeutically effective amount" to tumour cells in a subject.

Preferably, the nitroreductase enzyme is encoded for by the nfsB gene of either *E. Coli* or by *Clostridia* species.

In a fifth aspect, the present invention provides a method for the use as prodrugs suitable for GDEPT (gene-dependent enzyme-prodrug therapy) in conjunction with at least one nitroreductase enzyme, as an anticancer agent including the step of administering a compound of Formula I as defined above or a compound of Formulae Ia-Ic, IIa-IIc and IIIa-c as defined above or a mixture thereof in a "therapeutically effective amount" to target tumour cells in a subject.

Preferably the nitroreductase enzyme is encoded for by the nfsB gene of either *E. Coli* or by *Clostridia* species.

In a sixth aspect of the present invention, there is provided a method of cell ablation therapy utilising at least one nitroreductase enzyme, wherein the method includes the step of administering a compound of Formula I as defined above or a compound of Formulae Ia-Ic, IIa-IIc and IIIa-c as defined above or a mixture thereof in a "therapeutically effective amount" to ablate tumour cells in tissue in a subject, wherein said tissue expresses the at least one nitroreductase enzyme.

Preferably the nitroreductase enzyme is encoded for by the nfsB gene of either *E. Coli* or by *Clostridia* species.

Preferably, the cell ablation therapy provides a substantially minimal bystander effect.

In a seventh aspect of the present invention there is provided a pharmaceutical composition including a therapeutically effective amount of a compound of formula I or a compound of formulae Ia-c, IIa-c, IIIa-c or a mixture thereof, and a pharmaceutically acceptable excipient, adjuvant, carrier, buffer or stabiliser.

The pharmaceutically acceptable excipient, adjuvant, carrier, buffer or stabiliser should preferably be non-toxic and should not interfere with the efficacy of the active ingredient. The precise nature of the carrier or other material will depend on the route of administration, which may be oral, or by injection, such as cutaneous, subcutaneous, or intravenous. It is to be appreciated that these factors could be readily determined by someone skilled in the art without undue experimentation.

Pharmaceutical compositions for oral administration may be in tablet, capsule, powder or liquid form. A tablet may comprise a solid carrier or an adjuvent. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin.

For intravenous, cutaneous or subcutaneous injection, the active ingredient will be in the form of a parenterally acceptable aqueous solution which is pyrogen-free and has a suitable pH, isotonicity and stability. Those of relevent skill in the art are well able to prepare suitable solutions using, for example, isotonic vehicles such as Sodium Chloride injection, Ringer's injection, Lactated Ringer's injection. Preservatives, stabilisers, buffers antioxidants and/or other additives may be included as required.

In an eighth aspect of the present invention there is provided, the use in the manufacture of a medicament of an effective amount of a compound of Formula I as defined above or of Formulae Ia-Ic, IIa-IIc and IIIa-c as defined above, for use in GDEPT to target cancer cells in a subject in need thereof.

In a ninth aspect of the present invention there is provided, the use in the manufacture of a medicament of an effective amount of a compound of Formula I as defined above or a compound of Formulae Ia-Ic, IIa-IIc and IIIa-c as defined above, for use in cell ablation therapy to target cancer cells in a subject in need thereof.

While the compounds of the present invention will typically be used to target tumour cells or tumour tissues in human subjects, they may be used to target tumour cells or tissues in other warm blooded animal subjects such as other primates, farm animals such as cattle, and sports animals and pets such as horses, dogs, and cats.

As used throughout the specification the term "therapeutically effective amount", is to be understood as an amount of a compound of Formula I as defined above or a compound of any one of compounds Ia-c, IIa-c and IIIa-c as defined above or a mixture thereof that is sufficient to show benefit to a subject with cancer cells. The actual amount, rate and time-course of administration, will depend on the nature and severity of the disease being treated. Prescription of treatment is within the responsibility of general practitioners and other medical doctors.

It is to be understood that the compounds of the invention as defined above may be administered alone or in combination with other treatments, especially radiotherapy, either simultaneously or sequentially dependent upon the condition to be treated.

As used throughout the specification the pharmaceutically acceptable derivatives and salts thereof include acid derived salts formed from are hydrochloric, sulfuric, phosphoric, acetic, citric, oxalic, malonic, salicylic, malic, fumaric, succinic, ascorbic, maleic, methanesulfonic, isethionic acids and the like and base derived salts formed from sodium and potassium carbonate, sodium and potassium hydroxide, ammonia, triethylamine, triethanolamine and the like.

The technique of cell ablation therapy, would be known to someone skilled in the art. This therapy can be used to selectively ablate specified target cells or tissue through specific enzymatic expression of a nitroreductase for example, that is specifically expressed by the tissue and which can then be employed to active a prodrug into an active metabolite to ablate the specified target cells or tissue. (Gusterson et al. *Endocrine Related Cancer*, 1997, 4, 67-74.)

The expression "substantially minimal bystander effect" is to be understood as meaning that the killing of adjoining non-targeted tumour cells is minimal as a result of diffusion between the targeted tumour cells and non-targeted tumour cells of an activated metabolite that arises from the enzymatic activation of a compound of Formula I as defined above or a compound of any one of compounds Ia-c, IIa-c and IIIa-c as defined above or a mixture thereof.

Further aspects of the present invention will become apparent from the following description given by way of example only and with reference to the accompanying synthetic schemes.

DETAILED DESCRIPTION OF THE INVENTION

The compounds of formula (I) and the acid addition salts and N-oxides thereof may be prepared by the processes outlined in Schemes 1-3, examples of which are found in Examples A-C.

Scheme 1.

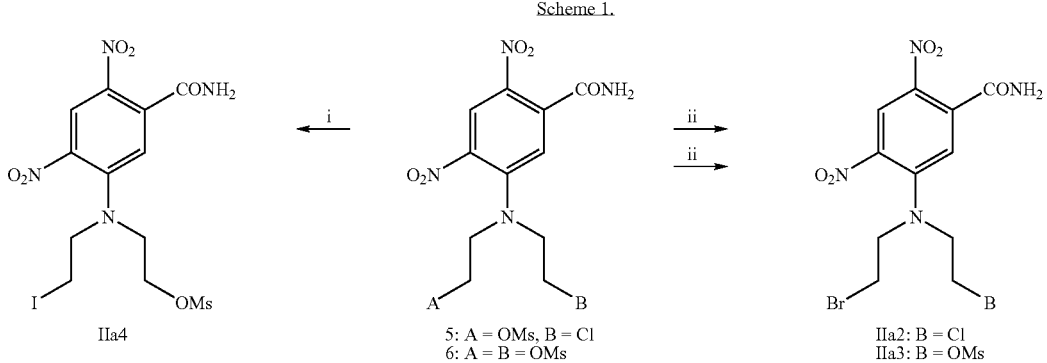

IIa4

5: A = OMs, B = Cl
6: A = B = OMs

IIa2: B = Cl
IIa3: B = OMs

-continued
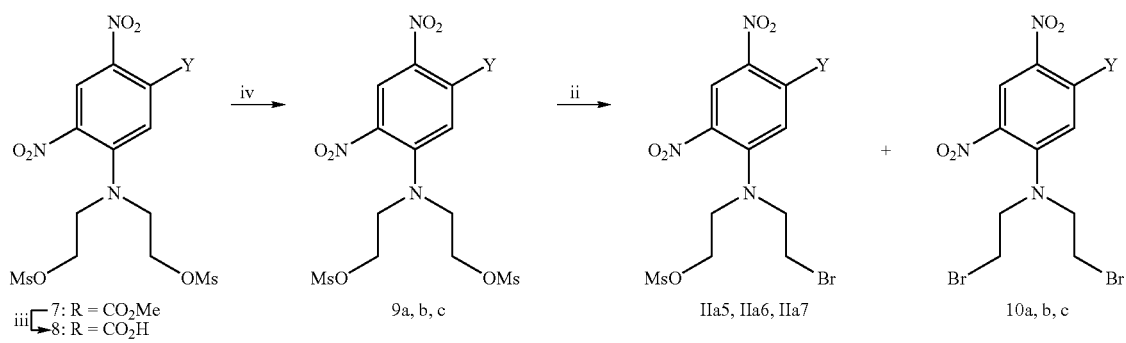
Reagents:
(i) NaI/DMF;
(ii) LiBr/MeCN;
(iii) KOH;
(iv) SOCl$_2$, then RNH$_2$.
a: Y = (CH$_2$)$_2$OH
b: Y = (CH$_2$)$_3$OH
c: Y = CH$_2$CH(OH)CH$_2$OH
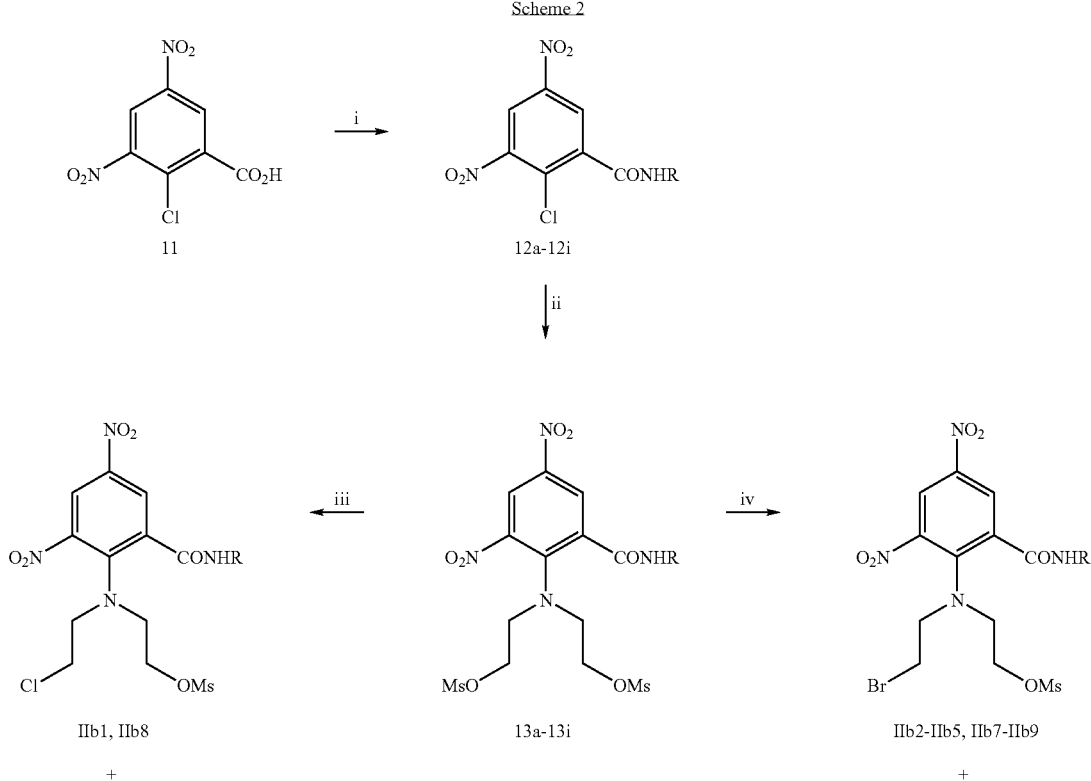

-continued

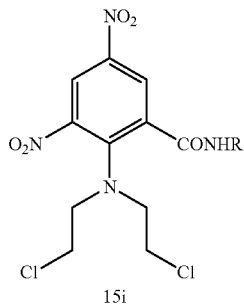

15i

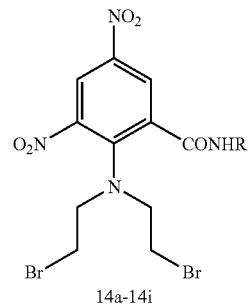

14a-14i

Reagents:
(i) RNH$_2$;
(ii) HN(CH$_2$CH$_2$OH)$_2$, then MsCl;
(iii) LiCl;
(iv) LiBr.
a: R = H
b: R = (CH$_2$)$_2$OH
c: R = (CH$_2$)$_2$OTHP
d: R = (CH$_2$)$_3$OH
e: R = (CH$_2$)$_3$OTHP
f: R = CH$_2$CH(OH)CH$_2$OH
g: R = h: R = (CH$_2$)$_3$Nmorpholide
i: R = (CH$_2$)$_2$CO$_2$Me

Scheme 3.

16: Y = CO$_2$Me
17: Y = CO$_2$H 18a-18f

IIc1, IIc3, IIc5, IIc7

IIc2, IIc4, IIc6, IIc8-IIc10

19a-f

Reagents:
(i) KOH; then HCl
(ii) SOCl$_2$, then NH$_4$OH, then HCl
(iii) LiBr
a: R = H
b: R = (CH$_2$)$_2$OH
c: R = (CH$_2$)$_3$OH
d: R = (CH$_2$)$_4$OH
e: R = CH$_2$CH(OH)CH$_2$OH
f: R = (CH$_2$)$_3$Nmorpholide In Schemes 1-3, the key reaction is reaction of the dimesylates 6, 9, 13a-13g and 18a-18d with strictly controlled amounts of LiBr or NaI in a polar solvent like DMF or MeCN to give the unsymmetrical bromo- and iodo-mesylate mustards. The method can also be adapted to reaction of the known chloromesylate (5) to give the unsymmetrical chloro/bromo mustard IIa2. While this reaction gives varying amounts of the corresponding bis(bromo) or bis(iodo) compounds as well, these can be easily separated by chromatography to give the pure unsymmetrical mustards.

Compounds of formula I wherein X represents $SO_2Me$, Y represents $CONR^2R^3$, and A and B each independently represent halogen or $OSO_2R^4$ (with the proviso that A≠B) can be prepared by the general route outlined (for a specific example) in Scheme 4, from 3,4-difluorobenzonitrile [after Atwell et al., *Anti-Cancer Drug Design*, 1996, 11, 553-567]. Reaction of this with NaSMe followed by oxidation provides the $SO_2Me$ group, and the nitrile is then elaborated to the $CONR^2R^3$ function. Displacement of the 4-F group with diethanolamine, followed by elaboration, gives the required asymmetric mustards.

Compounds of formula I wherein X represents CN, Y represents $CONR^2R^3$, and A and B each independently represent halogen or $OSO_2R^4$ (with the proviso that A≠B) can be prepared by the general route outlined (as shown for a specific example) in Scheme 5, from 3,4-difluorobenzonitrile [after Atwell et al., *Anti-Cancer Drug Design*, 1996, 11, 553-567]. Conversion of the nitrile to a carboxamide (hydrolysis followed by amination), then displacement of the 3-F with TMS-CN, followed by reaction of the 4-F group with diethanolamine and subsequent elaboration as in Scheme 4 gives the required asymmetric mustard.

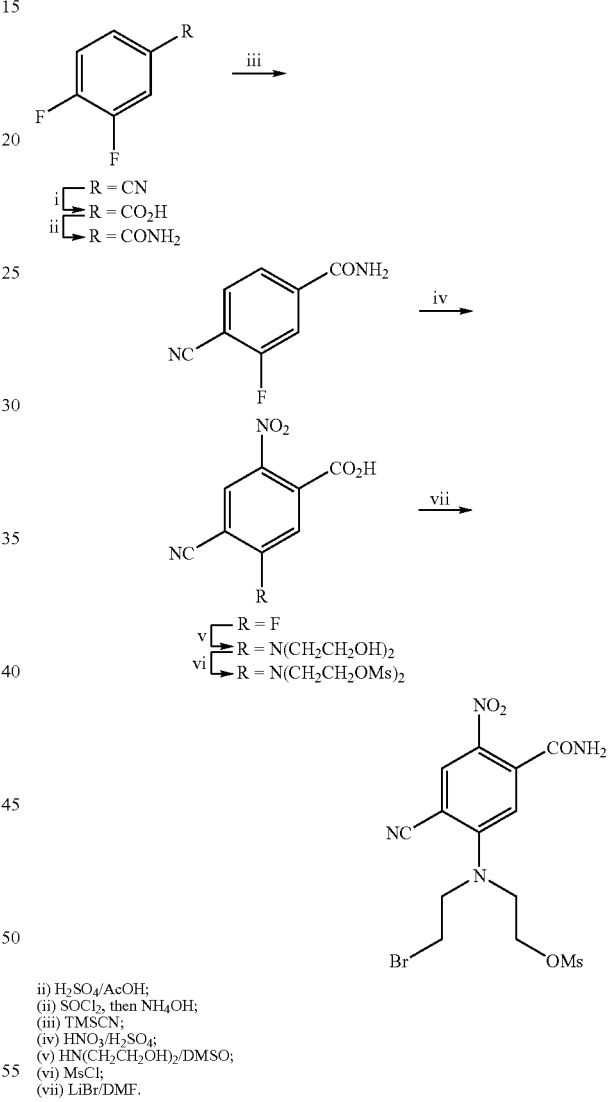

Scheme 5 ii) $H_2SO_4$/AcOH;
(ii) $SOCl_2$, then $NH_4OH$;
(iii) TMSCN;
(iv) $HNO_3$/$H_2SO_4$;
(v) $HN(CH_2CH_2OH)_2$/DMSO;
(vi) MsCl;
(vii) LiBr/DMF.

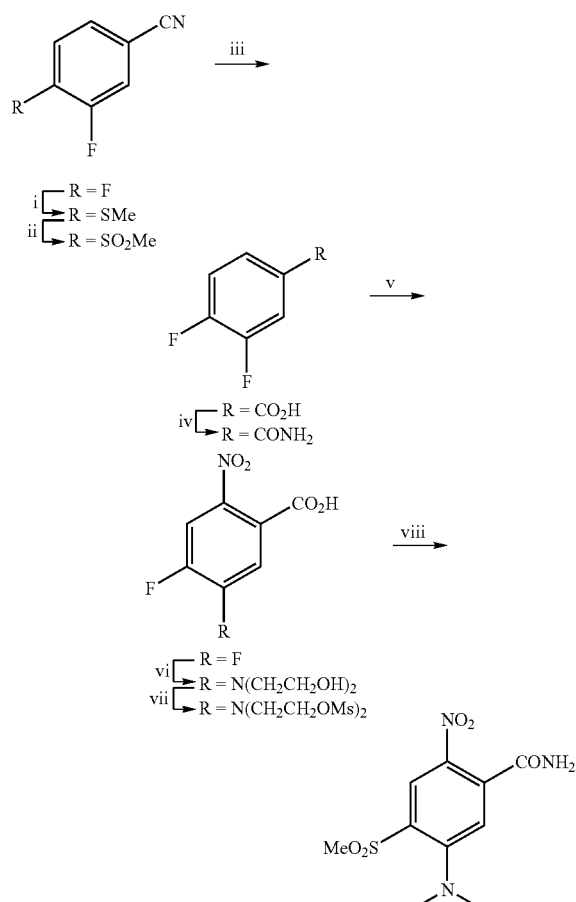

Scheme 4

(i) NaSMe;
(ii) $NaBO_3$;
(iii) $H_2SO_4$/AcOH;
(iv) $SOCl_2$, then $NH_4OH$;
(v) $HNO_3$/$H_2SO_4$;
(vi) $HN(CH_2CH_2OH)_2$/DMSO;
(vii) MsCl;
(viii) LiBr/DMF.

Compounds of formula I wherein X represents $NO_2$, Y represents $NHCOR^2$, and A and B each independently represent halogen or $OSO_2R^4$ (with the proviso that A≠B) can be prepared by the general route outlined (as shown for a specific example) in Scheme 6, from 2,4-dinitro-5-chlorobenzoic acid. Curtius reaction with DPPA, followed by hydrolysis and acetylation gives the acetamide. Reaction of the 5-Cl group with diethanolamine and subsequent elaboration as in Scheme 4 gives the required asymmetric mustard.

Scheme 6

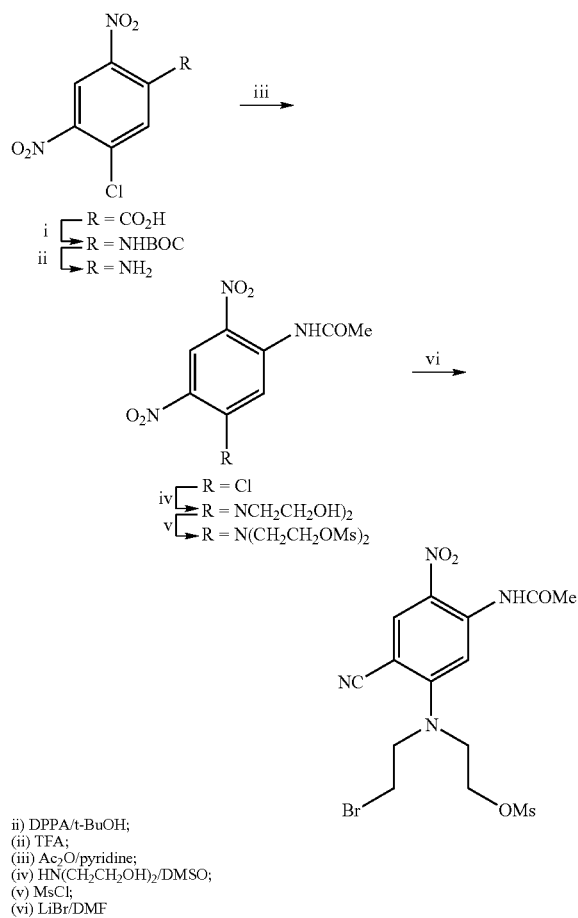

ii) DPPA/t-BuOH;
(ii) TFA;
(iii) Ac₂O/pyridine;
(iv) HN(CH₂CH₂OH)₂/DMSO;
(v) MsCl;
(vi) LiBr/DMF Compounds of formula I wherein X represents NO$_2$, Y represents OR$^2$, and A and B each independently represent halogen or OSO$_2$R$^4$ (with the proviso that A≠B) can be prepared by the general route outlined (as shown for a specific example) in Scheme 7, from 1,5-dichloro-2,4-dinitrobenzene. Reaction of the more active 1-Cl group with NaOMe gives the methyl ether, and subsequent elaboration of the 5-Cl group as in Scheme 4 gives the required asymmetric mustard.

Scheme 7

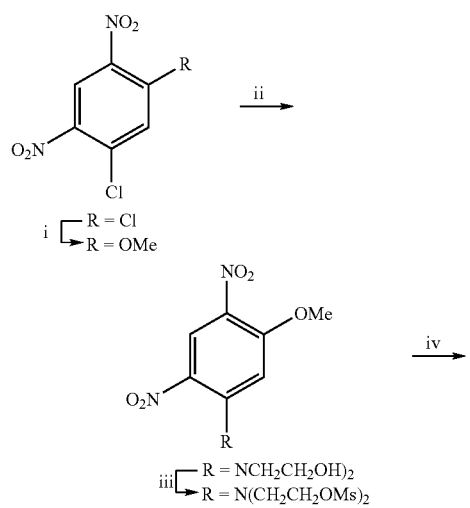

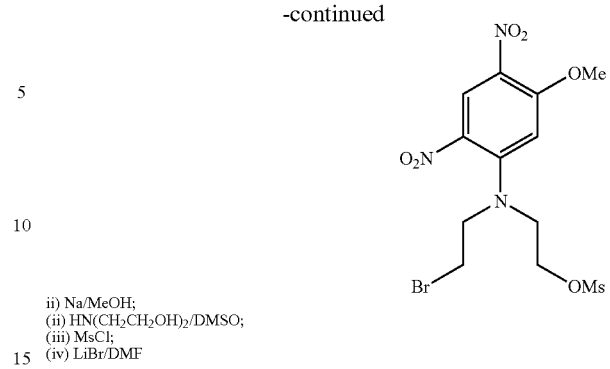

ii) Na/MeOH;
(ii) HN(CH₂CH₂OH)₂/DMSO;
(iii) MsCl;
(iv) LiBr/DMF

Compounds of formula I wherein X represents NO$_2$, Y represents SO$_2$NHR$^2$, and A and B each independently represent halogen or OSO$_2$R$^4$ (with the proviso that A≠B) can be prepared by the general route outlined (as shown for a specific example) in Scheme 8, from 5-chloro-2,4-dinitroaniline (see Scheme 6). Diazotization followed by oxidation and amination provides the sulphonamide [Herbert R B & Hollman R G. *Tetrahedron* 1965, 21, 663-675], and subsequent elaboration of the 5-Cl group as in Scheme 4 gives the required asymmetric mustard.

Scheme 8

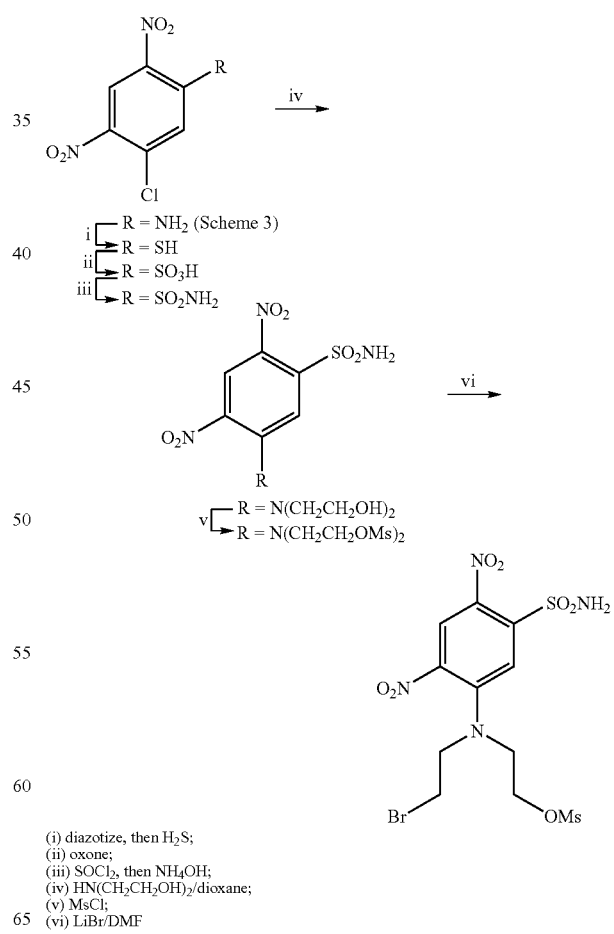

(i) diazotize, then H₂S;
(ii) oxone;
(iii) SOCl₂, then NH₄OH;
(iv) HN(CH₂CH₂OH)₂/dioxane;
(v) MsCl;
(vi) LiBr/DMF The following Table 1 sets out physicochemical data for 25 compounds within the general formula I, representative of it, and preparable by the processes of the invention.

TABLE 1

(IIa)  (IIb)  (IIc)

| No | Y | X | A | B | PRIOR ART COMPOUND |
|---|---|---|---|---|---|
| 5 | CONH$_2$ | NO$_2$ | Cl | OMs | [Friedlos et al., J. Med Chem. 1997, 40, 1270] |

| No | Y | X | A | B | mp (° C.) | formula | analyses |
|---|---|---|---|---|---|---|---|
| *Examples of formula IIa* | | | | | | | |
| IIa2 | CONH$_2$ | NO$_2$ | Cl | Br | 153 | C$_{11}$H$_{12}$BrClN$_4$O$_5$ | C, H, N, Cl |
| IIa3 | CONH$_2$ | NO$_2$ | Br | OMs | 160-161 | C$_{12}$H$_{15}$BrN$_4$O$_8$S | C, H, N, Br |
| IIa4 | CONH$_2$ | NO$_2$ | I | OMs | 160 | C$_{12}$H$_{15}$IN$_4$O$_8$S | C, H, N, I |
| IIa5 | CONH(CH$_2$)$_2$OH | NO$_2$ | Br | OMs | 102-104 | C$_{14}$H$_{19}$Br$_4$N$_4$O$_9$S | C, H, N, Br |
| IIa6 | CONH(CH$_2$)$_3$OH | NO$_2$ | Br | OMs | gum | C$_{15}$H$_{21}$Br$_4$N$_4$O$_9$S | HRMS |
| IIa7 | CONHCH$_2$CH(OH)—CH$_2$OH | NO$_2$ | Br | OMs | 117-118 | C$_{15}$H$_{21}$BrN$_4$O$_{10}$S | C, H, N, Cl |
| *Examples of formula IIb* | | | | | | | |
| IIb1 | CONH$_2$ | NO$_2$ | Cl | OMs | 155-157 | C$_{12}$H$_{15}$ClN$_4$O$_8$S | C, H, N, Cl |
| IIb2 | CONH$_2$ | NO$_2$ | Br | OMs | 153-154 | C$_{12}$H$_{15}$BrN$_4$O$_8$S | C, H, N, Br |
| IIb3 | CONH(CH$_2$)$_2$OH | NO$_2$ | Br | OMs | gum | C$_{14}$H$_{19}$BrN$_4$O$_9$S | HRMS |
| IIb4 | CONH(CH$_2$)$_2$OH | NO$_2$ | I | OMs | gum | C$_{14}$H$_{19}$IN$_4$O$_9$S | |
| IIb5 | CONH(CH$_2$)$_3$OH | NO$_2$ | Br | OMs | oil | C$_{15}$H$_{21}$BrN$_4$O$_9$S | |
| IIb6 | CONHCH$_2$CH(OH)—CH$_2$OH | NO$_2$ | Br | OMs | gum | C$_{15}$H$_{21}$BrN$_4$O$_{10}$S | C, H, N, Br |
| IIb7 | CONH(CH$_2$)$_3$Nmorph | NO$_2$ | Br | OMs | gum | C$_{19}$H$_{28}$BrN$_5$O$_9$S | HRMS |
| IIb8 | CONH(CH$_2$)$_2$CO$_2$Me | NO$_2$ | Cl | OMs | oil | C$_{16}$H$_{21}$ClN$_4$O$_{10}$S | HRMS |
| IIb9 | CONH(CH$_2$)$_2$CO$_2$Me | NO$_2$ | Br | OMs | gum | C$_{16}$H$_{21}$BrN$_4$O$_{10}$S | HRMS |
| *Examples of formula IIc* | | | | | | | |
| IIc1 | CONH$_2$ | NO$_2$ | Cl | OMs | 134-136 | C$_{12}$H$_{15}$ClN$_4$O$_8$S | C, H, N, S |
| IIc2 | CONH$_2$ | NO$_2$ | Br | OMs | 143-145 | C$_{12}$H$_{15}$BrN$_4$O$_8$S | C, H, N, Br |
| IIc3 | CONH(CH$_2$)$_2$OH | NO$_2$ | Br | OMs | 94-97 | C$_{14}$H$_{19}$BrN$_4$O$_9$S | C, H, N |
| IIc4 | CONH(CH$_2$)$_3$OH | NO$_2$ | Cl | OMs | 104-109 | C$_{15}$H$_{21}$ClN$_4$O$_9$S | C, H, N, Cl |
| IIc5 | CONH(CH$_2$)$_3$OH | NO$_2$ | Br | OMs | 115-117 | C$_{15}$H$_{21}$BrN$_4$O$_9$S | C, H, N |
| IIc6 | CONH(CH$_2$)$_4$OH | NO$_2$ | Br | OMs | 114-117 | C$_{16}$H$_{23}$BrN$_4$O$_9$S | C, H, N |
| IIc7 | CONHCH$_2$CH(OH)—CH$_2$OH | NO$_2$ | Cl | OMs | 100-105 | C$_{15}$H$_{21}$ClN$_4$O$_{10}$S | C, H, N, Cl |
| IIc8 | CONH$_2$CH$_2$CH(OH)CH$_2$OH | NO$_2$ | Br | OMs | 108-110 | C$_{15}$H$_{21}$BrN$_4$O$_{10}$S | C, H, N, Br |
| IIc9 | CONH(CH$_2$)$_3$Nmorph | NO$_2$ | Cl | OMs | 113-116 | C$_{19}$H$_{28}$ClN$_5$O$_9$S | HRMS |
| IIc10 | CONH(CH$_2$)$_3$Nmorph | NO$_2$ | Br | OMs | 114-117 | C$_{19}$H$_{28}$BrN$_5$O$_9$S | HRMS |

The following Examples A-C illustrate the preparation of compounds representative of the general formula (I).

Example A

Preparation of Analogues of Class IIa by the Method Outlined in Scheme 1

5-[(2-Bromoethyl)(2-chloroethyl)amino]-2,4-dinitrobenzamide (IIa2).

A mixture of 2-[5-(aminocarbonyl)(2-chloroethyl)-2,4-dinitroanilino]ethyl methanesulfonate (5) [Friedlos et al., *J. Med. Chem.* 1997, 40, 1270] (0.91 g, 2.2 mmol) and LiBr (0.21 g, 2.4 mmol) in anhydrous MeCN (25 mL) was stirred under reflux for 1.5 h, then concentrated under reduced pressure. The residue was chromatographed on silica gel, eluting with CH$_2$Cl$_2$/EtOAc (3:2) to give a crude product contaminated with the corresponding dibromo mustard. Purification by multiple recrystallisations from EtOAc/I—Pr$_2$O gave IIa2 (595 mg, 68%):

mp 153° C.; $^1$H NMR [(CD$_3$)$_2$SO] δ 8.52 (s, 1H, H-3), 8.17 & 7.82 (2×s, 2H, CONH$_2$), 7.43 (s, 1H, H-6), 3.82 (t, J=5.8 Hz, 2H, CH$_2$Cl), 3.77-3.63 (m, 6H, N(CH$_2$—)CH$_2$CH$_2$Br). Anal. Calc for C$_{11}$H$_{12}$BrClN$_4$O$_5$: C, 33.4; H, 3.1; N, 14.2; Cl, 9.6. Found: C, 33.4; H, 3.0; N, 14.1; Cl, 8.9%.

2-[5-(Aminocarbonyl)(2-bromoethyl)-2,4-dinitroanilino]ethyl methanesulfonate (IIa3).

A mixture of 2-(5-(aminocarbonyl){2-[(methylsulfonyl)oxy]ethyl}-2,4-dinitroanilino)ethyl methanesulfonate (6) [Friedlos et al., *J. Med. Chem.*, 1997, 40, 1270] (1.60 g, 3.4 mmol) and LiBr (356 mg, 4.1 mmol) in anhydrous MeCN (30 mL) was stirred under reflux for 1 h The mixture was concentrated under reduced pressure and the residue was chromatographed on silica gel. Elution with EtOAc/$CH_2Cl_2$ (11:9) gave the dibromo mustard, while further elution with EtOAc/$CH_2Cl_2$ (3:1) gave IIa3 (0.61 g, 39%): mp (EtOAc/I—$Pr_2O$) 160-161° C.; $^1$H NMR [($CD_3$)$_2$SO] δ 8.53 (s, 1H, H-3), 8.14 & 7.83 (2×s, 2H, $CONH_2$), 7.46 (s, 1H, H-6), 4.33 (t, J=5.1 Hz, 2H, $CH_2O$), 3.74 (t, J=5.1 Hz, 2H, $CH_2CH_2O$), 3.70 (br s, 4H, $CH_2CH_2Br$), 3.14 (s, 3H, $CH_3$). Anal. Calcd for $C_{12}H_{15}BrN_4O_8S$: C, 31.7; H, 3.3; N, 12.3; Br, 17.6. Found: C, 32.0; H, 3.4; N, 12.2; Br, 17.7%.

2-[5-(Aminocarbonyl)(2-iodoethyl)-2,4-dinitroanilino]ethyl methanesulfonate (IIa4).

A mixture of 6 (1.12 g, 2.38 mmol) and NaI (0.46 g, 3.07 mmol) in anhydrous MeCN (20 mL) was stirred at reflux for 1 h. The mixture was concentrated under reduced pressure and the residue was chromatographed on silica gel. Elution with EtOAc/$CH_2Cl_2$ (1:1) gave the diiodo mustard, while further elution with EtOAc/$CH_2Cl_2$ (3:1) gave IIa4 (0.49 g, 41%): mp ($Me_2CO$/EtOAc/I—$Pr_2O$) 160° C.; $^1$H NMR [($CD_3$)$_2$SO] δ 8.52 (s, 1H, H-3), 8.14 & 7.83 (2×s, 2H, $NH_2$), 7.44 (s, 1H, H-6), 4.33 (t, J=5.1 Hz, 2H, $CH_2O$), 3.73 (t, J=5.1 Hz, 2H, $CH_2CH_2O$), 3.65 (t, J=6.9 Hz, 2H, $CH_2CH_2I$), 3.40 (t, J=6.9 Hz, 2H, $CH_2I$), 3.13 (s, 3H, $CH_3$). Anal. Calcd for $C_{12}H_{15}IN_4O_8S$: C, 28.7; H, 3.0; N, 11.2; I, 25.3. Found: C, 29.4; H, 3.0; N, 11.0; I, 25.0%.

2-((2-Bromoethyl)5-{[(2-hydroxyethyl)amino]carbonyl}-2,4-dinitroanilino)ethyl methanesulfonate (IIa5).

A stirred solution of methyl 5-[bis(2-hydroxyethyl)amino]-2,4-dinitrobenzoate [Palmer et al., *J. Med. Chem* 1994, 37, 2175] (5.50 g, 16.7 mmol) and $Et_3N$ (5.82 mL, 41.8 mmol) in dry $CH_2Cl_2$ (50 mL) was treated dropwise at 0° C. with MsCl (3.14 mL, 40.0 mmol). After 30 min, 10% aqueous $KHCO_3$ (100 mL) was added, and the mixture was stirred for a further 30 min at 0° C. and then diluted with pet. ether (500 mL). The precipitated product was collected and washed with water and iPr$_2$O to give methyl 5-(bis{2-[(methylsulfonyl)oxy]ethyl}amino)-2,4-dinitrobenzoate (7) (7.44 g, 92%): mp ($CH_2Cl_2$/pet. ether) 157-158° C.; $^1$H NMR [($CD_3$)$_2$SO} δ 8.62 (s, 1H, H-3), 7.77 (s, 1H, H-6), 4.35 (t, J=5.1 Hz, 4H, 2×$CH_2O$), 3.88 (s, 3H, $CO_2CH_3$), 3.73 (t, J=5.1 Hz, 4H, N($CH_2$)$CH_2$), 3.13 (s, 6H, 2×$SO_2CH_3$). Anal calcd for $C_{14}H_{19}N_2O_{12}S_2$: C, 34.6; H, 3.9; N, 8.7; S, 13.2. Found: C, 34.8; H, 3.7; N, 8.9; S, 13.1%.

Hydrolysis of 7 (3.0 g, 6.18 mmol) with 3 N KOH (40 mL) in dioxane (200 mL) at room temperature for 15 min followed by acidification with 1N HCl and extraction with EtOAc gave a quantitative yield of 5-(bis{2-[(methylsulfonyl)oxy]ethyl}amino)-2,4-dinitrobenzoic acid (8), mp 200-210° C., which was used for the next step without further purification; $^1$H NMR [($CD_3$)$_2$SO] δ 14.1 (v br s, 1H, $CO_2H$), 8.57 (s, 1H, H-3), 7.69 (s, 1H, H-6), 4.34 (t, J=5.1 Hz, 4H, 2×$CH_2O$), 3.72 (t, J=5.1 Hz, 4H, 2×$CH_2CH_2O$), 3.13 (s, 6H, 2×$CH_3$).

A suspension of 8 (3.20 g, 6.79 mmol) in $SOCl_2$ (60 mL) containing DMF (2 drops) was heated under reflux for 1 h. Evaporation of the solvent under reduced pressure, followed by azeotroping in with benzene gave the crude acid chloride, which was dissolved in dry $Me_2CO$ (80 mL) and treated at 0° C. with 2-aminoethanol (1.24 g, 20.3 mmol). After stirring at 0° C. for 5 min, the mixture was acidified to pH 2-3 with 0.2 N HCl, concentrated to half volume, and then solid NaBr was added. The mixture was extracted with EtOAc (2×) and the combined extracts were washed with saturated NaBr solution, dried ($Na_2SO_4$) and evaporated. The residue was chromatographed on silica gel, eluting with EtOAc/MeOH (15:1) to give 2-(5-{[(2-hydroxyethyl)amino]carbonyl} {2-[(methylsulfonyl)oxy]ethyl}-2,4-dinitroanilino)ethyl methanesulfonate (9a) (2.87 g, 82%) as a gum that was used directly.

A mixture of 9a (1.80 g, 3.50 mmol) and LiBr (0.43 g, 4.95 mmol) in DMF (5 mL) was stirred at 60° C. for 2 h. The reaction was then poured into saturated NaBr solution and extracted with EtOAc (2×). The combined extracts were washed with saturated NaBr solution, dried ($Na_2SO_4$) and concentrated under reduced pressure. The residue was chromatographed on silica gel, eluting with EtOAc, to give 5-[bis(2-bromoethyl)amino]-N-(2-hydroxyethyl)-2,4-dinitrobenzamide (10a) (0.78 g, 46%): mp (MeOH/EtOAc/pet. ether) 151-152° C.; $^1$H NMR [($CD_3$)$_2$SO] δ 8.73 (t, J=5.7 Hz, 1H, CONH), 8.53 (s, 1H, H-3), 7.43 (s, 1H, H-6), 4.76 (t, J=5.6 Hz, 1H, OH), 3.77-3.64 (m, 8H, N($CH_2CH_2Br$)$_2$), 3.53 (q, J=6.0 Hz, 2H, $CH_2OH$), 3.31 (q, partially obscured, J=6.1 Hz, 2H, $CONHCH_2$). Anal. calcd for $C_{13}H_{16}Br_2N_4O_6$): C, 32.3; H, 3.3; 11.6; 33.0. Found: C, 32.6; H, 3.3; N, 11.6; Br, 33.3%.

Further elution with EtOAc/MeOH (9:1) gave IIa5 (0.73 g, 42%): mp (EtOAc) 102-104° C.; $^1$H NMR [($CD_3$)$_2$SO] δ 8.70 (t, J=5.7 Hz, 1H, CONH), 8.54 (s, 1H, H-3), 7.46 (s, 1H, H-6), 4.76 (J=5.5 Hz, 1H, OH), 4.34 (t, J=5.1 Hz, 2H, $CH_2OSO_2$), 3.74 (t, J=5.1 Hz, 2H, $CH_2CH_2OSO_2$), 3.70 (br s, 4H, $CH_2CH_2Br$), 3.53 (q, J=6.0 Hz, 2H, $CH_2OH$), 3.31 (q, partially obscured, J=6.1 Hz, 2H, $CONHCH_2$), 3.14 (s, 3H, $CH_3$). Anal. calcd for $C_{14}H_{19}BrN_4O_9S$: C, 34.3; H, 3.9; N, 11.0; Br, 15.9. Found: C, 33.8; H, 3.8; H, 11.2; Br, 16.0%.

2-((2-Bromoethyl)5-{[(3-hydroxypropyl)amino]carbonyl}-2,4-dinitroanilino)ethyl methanesulfonate (IIa6).

5-(Bis {2-[(methylsulfonyl)oxy]ethyl}amino)-2,4-dinitrobenzoic acid (8) was heated under reflux in excess $SOCl_2$ (60 mL) and catalytic DMF for 1 h. Evaporation under reduced pressure, followed by azeotroping in benzene, gave the crude acid chloride. This was dissolved in dry $Me_2CO$ and treated at 0° C. with 3-amino-1-propanol at 0° C. for 5 min. The mixture was acidified to pH 2-3 with 0.2 N HCl, concentrated to half volume, and then solid NaBr was added, followed by extraction with EtOAc (2×). Evaporation, and chromatography of the residue on silica gel, eluting with EtOAc/MeOH (9:1), gave 2-(5-{[(3-hydroxypropyl)amino]carbonyl}{2-[(methylsulfonyl)oxy]ethyl}-2,4-dinitroanilino)ethyl methanesulfonate (9b) (68%) as a yellow gum;

$^1$H NMR [($CD_3$)$_2$SO] δ 8.54 (t, J=5.7 Hz, 1H), 8.53 (s, 1h), 7.45 (s, 1H), 4.43 (t, J=5.1 Hz, 1H), 4.33 (t, J=5.2 Hz, 4H), 3.69 (t, J=5.2 Hz, 4H), 3.57 (q, J=5.9 Hz, 2H), 3.26 (after $D_2O$ exchange, t, J=7.0 Hz, 1H), 3.12 (s, 6H), 1.66 (pent, J=6.7 Hz, 2H). HRMS (FAB) calcd. for $C_{16}H_{25}N_4O_{12}S$ (MH$^+$) m/z 529.0910; found 529.0904.

A solution of 9b in DMF was treated with LiBr (1.4 equiv.), and worked up as above, and the product was chromatographed on silica gel. Elution with EtOAc gave a small amount of the dibromo mustard 10b, while elution with EtOAc/MeOH (19:1) gave IIa6 (31%) as a yellow gum:

$^1$H NMR [($CD_3$)$_2$SO] δ 8.60 (t, J=5.6 Hz, 1H), 8.54 (s, 1H), 7.44 (s, 1H), 4.45 (t, J=5.2 Hz, 1H), 4.33 (t, J=5.1 Hz, 2H), 3.74 (t, J=5.2 Hz, 2H), 3.72-3.66 (m, 4H), 3.49 (q, J=5.9 Hz, 2H), 3.27 (after $D_2O$ exchange, t, J=7.0 Hz, 2H), 3.14 (s, 3H), 1.68 (pent, J=6.7 Hz, 2H). HRMS (FAB) calcd. for $C_{15}H_{22}^{79}BrN_4O_9S$ (MH$^+$) m/z 515.0270; found 515.0283.

2-((2-Bromoethyl)-5-{[(2,3-dihydroxypropyl)amino]carbonyl}-2,4-dinitroanilino)ethyl methanesulfonate (IIa7).

Reaction of the crude acid chloride made as above from acid 8 (2.9 g, 6.15 mmol) was dissolved in Me$_2$CO (100 mL), cooled in an ice-bath and treated with an excess of 3-amino-1,2-propanediol. After string for 10 min. the reaction mixture was acidified to pH 2-3 with 1 N HCl, most of the solvent was evaporated, and the residue was partitioned between water and EtOAc. The aqueous layer was re-extracted with EtOAc and the combined organic phases were dried and evaporated. The residue was adsorbed directly onto silica gel and chromatographed, elution with EtOAc/MeOH (from 50:1 to 10:1) giving 2-(5-{[(2,3-dihydroxypropyl)amino]carbonyl}{2-[(methylsulfonyl)oxy]ethyl}-2,4-dinitroanilino)ethyl methanesulfonate (9c) (2.92 g, 87%) as a yellow oil;

$^1$H NMR [(CD$_3$)$_2$SO] δ 8.66 (t, J=5.8 Hz, 1H, CONH), 8.54 (s, 1H, H-3), 7.48 (s, 1H, H-6), 4.81 (d, J=5.0 Hz, 1H, CHOH), 4.59 (t, J=5.1 Hz, 1H, CH$_2$O H), 4.35 (m, 4H, 2×CH$_2$OMs), 3.66 (m, 4H), 3.62 (m, 1H), 3.46-3.36 (m, 4H), 3.13 (s, 6H); $^{13}$C NMR δ 164.48; 147.09, 138.26, 137.27, 136.60, 124.17, 121.72, 70.02, 66.69, 63.68, 50.21, 42.68, 36.55. HRMS m/z (M+1)$^+$ required for $C_{16}H_{25}N_4O_{13}S_2$ 545.08596; Found 545.0856.

A solution of 9c (1.28 g, 2.53 mmol) was dissolved in EtOAc (100 mL) and treated with LiBr (347 mg, 4.0 mmol) at 60° C. for 2 h. Volatiles were removed under reduced pressure, and the residue was adsorbed directly onto silica gel and chromatographed. Elution with EtOAc/MeOH (from 1:0 to 10:2) gave 5-[bis(2-bromoethyl)amino]-N-(2,3-dihydroxypropyl)-2,4-dinitrobenzamide (10c) (0.4 g, 31%) as a foam;

$^1$H NMR [(CD$_3$)$_2$SO] δ 8.71 (t, J=5.8 Hz, 1H, CONH), 8.53 (s, 1H, H-3), 7.43 (s, 1H, H-6), 4.86 (d, J=5.0 Hz, 1H, CHOH), 4.59 (t, J=5.8 Hz, 1H, CH$_2$OH), 3.70-3.10 (m, 13H); $^{13}$C NMR δ 164.61, 146.65, 137.99, 137.35, 136.52, 124.25, 121.20, 70.05, 63.73, 52.44, 42.76, 30.33. HRMS m/z (M+1)$^+$ required for $C_{14}H_{19}^{79}Br_2N_4O_7$ 512.9621; Found 512.9596.

Further elution gave IIa7 (0.62 g, 46%):

mp (EtOAc) 117-118° C.; $^1$H NMR [(CD$_3$)$_2$SO] δ 8.68 (t, J=5.8 Hz, 1H, CONH), 8.53 (s, 1H, H-3), 7.46 (s, 1H, H-6), 4.82 (d, J=5.0 Hz, 1H, CHOH), 4.56 (t, J=5.1, 1H, CH$_2$OH), 4.32 (m, 2H, CH$_2$OMs), 3.75-3.60 (m, 7H), 3.46-3.36 (m, 4H), 3.13 (s, 3H); $^{13}$C NMR δ 164.48, 146.84, 138.05, 137.29, 136.52, 124.18, 121.40, 70.01, 66.74, 63.68, 52.89, 49.56, 42.69, 36.55, 30.20. Anal. Calcd for $C_{15}H_{21}BrN_4O_{10}S$: C, 34.1; H, 4.0; N, 10.6; Br, 15.0. Found: C, 34.0; H, 4.0; N, 10.5; Br, 15.2%.

Further elution gave starting material (9c) (0.27 g, 20%).

Example B

Preparation of Analogues of Class IIb by the Method Outlined in Scheme 2

2-[2-(Aminocarbonyl)(2-chloroethyl)-4,6-dinitroanilino] ethyl methanesulfonate (IIb1).

A solution of 2-[bis(2-hydroxyethyl)amino]-3,5-dinitrobenzamide [Friedlos et al., *J. Med. Chem,* 1997, 40, 1270] (2.5 g, 8 mmol) in CH$_2$Cl$_2$ (200 mL) was cooled in an ice-bath and Et$_3$N (8 mL) and MsCl (4 mL) were added in one portion. After stirred for 10 min, satd. NaHCO$_3$ (100 mL) was added, and after a further 30 min the aqueous phase was extracted with CH$_2$Cl$_2$ (2×70 mL), the combined organic phase were dried, concentrated under reduced pressure, and the residue was purified by column chromatography on silica gel. Elution with EtOAc/petroleum ether (1:1 to 1:0), gave IIb1 (0.6 g, 18%):

mp (EtOAc/petroleum ether) 155-157° C.; $^1$H NMR [(CD$_3$)$_2$SO] δ 8.74 (d, J=2.7 Hz, 1H, H-5), 8.34 (d, J=2.7 Hz, 1H, H-3), 8.19 (s, 1H, CONH), 7.99 (s, 1H, CONH), 4.29 (m, 2H, CH$_2$OMs), 3.73 (m, 2H, CH$_2$Cl), 3.48 (m, 4H, 2×CH$_2$N), 3.15 (s, 3H, OSO$_2$CH$_3$); $^{13}$C NMR δ 167.11, 145.98, 146.34, 140.84, 136.05, 127.26, 122.22, 67.49, 54.35, 51.34, 41.36, 36.46. Anal. Calcd for $C_{12}H_{15}ClN_4O_8S$: C, 35.1; H, 3.7; N, 13.7; Cl, 8.5. Found: C, 35.7; H, 3.9; N, 13.6; Cl, 8.7%. Further elution gave 2-(2-(aminocarbonyl){2-[(methylsulfonyl)oxy]ethyl}-4,6-dinitroanilino)ethyl methanesulfonate (13a) (3.0 g, 80%):

mp (EtOAc) 149-150° C.; $^1$H NMR [(CD$_3$)$_2$SO] δ 8.73 (d, J=2.8 Hz, 1H, H-5), 8.35 (d, J=2.9 Hz, 1H, H-3), 8.19 (s, 1H, CONH), 8.00 (s, 1H, CONH), 4.31 (m, 4H, 2×CH$_2$OMs), 3.49 (m, 4H, 2×CH$_2$—N), 3.14 (s, 6H, 2×OSO$_2$CH$_3$). Anal. Calcd for $C_{13}H_{18}N_4O_{11}S_2$: C, 33.2; H, 3.9; N, 11.9. Found: C, 33.7; H, 4.0; N, 11.8%.

2-[2-(Aminocarbonyl)(2-bromoethyl)-4,6-dinitroanilino] ethyl methanesulfonate (IIb2).

A solution of dimesylate 13a (1.62 g, 3.5 mmol) in warm EtOAc (100 mL) was treated with one portion of LiBr (400 mg, 4.7 mmol), and the mixture was heated to 60° C. for 2 h. Volatiles were removed under reduced pressure, and the residue was adsorbed directly onto silica gel and chromatographed. Elution with EtOAc/petroleum ether (1:1 to 1:0) gave the dibromide (0.31 g, 20%) as yellow solid. (lit., foam) [Friedlos et al., *J. Med. Chem.* 1997, 1270]. Further elution gave IIb2 (0.85 g, 53%):

mp (EtOAc/petroleum ether) 153-154° C.; $^1$H NMR [(CD$_3$)$_2$SO] δ 8.74 (d, J=2.8 Hz, 1H, H-5), 8.33 (d, J=2.8 Hz, 1H, H-3), 8.19 (s, 1H, CONH), 7.99 (s, 1H, CONH), 4.29 (m, 2H, CH$_2$OMs), 3.60 (m, 2H, CH$_2$Br), 3.49 (m, 4H, 2×CH$_2$—N), 3.14 (s, 3H, OSO$_2$CH$_3$); $^{13}$C NMR δ 167.11, 145.75, 146.37, 140.92, 136.12, 127.24, 122.20, 67.53, 54.41, 51.16, 36.46, 29.73. Anal. Calcd for $C_{12}H_{15}BrN_4O_8S$: C, 31.7; H, 3.3; N, 12.3; Br, 17.4. Found: C, 31.4; H, 3.4; N, 12.3; Br, 17.8%.

2-((2-Bromoethyl)-2-{[(2-hydroxyethyl)amino]carbonyl}-4,6-dinitroanilino)ethyl methanesulfonate (IIIb3).

2-Aminoethanol (2.9 g, 47 mmol) in 5 mL of water was added in one portion to a solution of crude 2-chloro-3,5-dinitrobenzoic acid chloride [prepared from 2-chloro-3,5-dinitrobenzoic acid 11 (5.0 g, 18.3 mmol) with SOCl$_2$] in Me$_2$CO (50 mL) while cooling in an ice-bath. The mixture was stirred for 30 min, then acidified with 1N HCl to pH4-5 and concentrated under reduced pressure to remove the Me$_2$CO. EtOAc (100 mL) was added, and after 2 h a white solid was collected, washed with EtOAc and air-dried to give 2-chloro-3,5-dinitro-N-(2-hydroxyethyl)benzamide (12b) (3.0 g, 36%):

mp (EtOAc) 159-160° C.; $^1$H NMR [(CD$_3$)$_2$SO] δ 8.99 (d, J=2.6 Hz, 1H, H-5), 8.86 (m, 1H, CONH), 8.56 (d, J=2.6 Hz, 1H, H-3), 4.83 (m, 1H, —OH), 3.54 (m, 4H) which was used for next step without further purification.

A solution of 12b (0.6 g, 2.14 mmol) in CH$_2$Cl$_2$ was cooled in an ice-bath, and 3,4-dihydro-2H-pyran (2.0 mL) and p-toluenesulfonic acid (0.1 g) were added. The reaction mixture was stirred for 2 h, then concentrated under reduced pressure. Chromatography of the residue on silica gel, eluting with EtOAc/petroleum ether (from 1:2 to 2:1), gave 2-chloro-3,5-dinitro-N-[2-(tetrahydro-2H-pyran-2-yloxy)ethyl]benzamide (12c) (0.8 g, 100%): as an oil;

¹H NMR [(CD₃)₂SO] δ 8.67 (d, J=2.6 Hz, 1H, H-4), 8.60 (d, J=2.6 Hz, 1H, H-6), 7.02 (m, 1H, CONH), 4.54 (m, 1H), 4.00-3.50 (m, 6H), 1.84-1.75 (m, 6H) which was used for next step without further purification. Reaction of 12c with diethanolamine, followed by MsCl/Et₃N as described above, gave 2-[{2-[(methylsulfonyl)oxy]ethyl}-4,6-dinitro-6-({[2-(tetrahydro-2H-pyran-2-yloxy)ethyl]amino}carbonyl)anilino] ethyl methanesulfonate (13c) (1.28 g, 100%): as a yellow foam;

¹H NMR [(CD₃)₂SO] δ 8.63 (d, J=2.9 Hz, 1H, H-5), 8.51 (d, J=2.9 Hz, 1H, H-3), 4.55 (m, 1H), 4.39 (m, 4H), 4.00-3.59 (m, 10H), 3.15 (s, 3H), 3.03 (s, 3H), 1.64-1.39 (m, 6H) which was used in the next step without further purification.

A solution of 13c (1.28 g, 2.14 mmol) in THF (60 mL) was treated with 1N HCl (40 mL), and the solution was stirred at 20° C. for 1 h, then diluted with water (100 mL), neutralized with satd. NaHCO₃, and extracted with EtOAc (3×80 mL). The combined organic phases were washed with brine and dried, the solvent was evaporated, and the residue was purified by chromatography on silica gel, eluting with EtOAc/MeOH (from 1:0 to 100:2), to give 13b (0.84 g, 76%): as a yellow foam;

¹H NMR [(CD₃)₂SO] δ 8.78 (m, 1H, CONH), 8.74 (d, J=2.7 Hz, 1H, H-5), 8.36 (d, J=2.7 Hz, 1H, H-3), 4.29 (m, 4H, 2×CH₂OMs), 3.56 (m, 2H), 3.45 (m, 6H), 3.14 (s, 6H, 2×OSO₂CH₃); ¹³C NMR δ 165.37, 146.27, 145.06, 140.63, 135.78, 127.62, 122.32, 67.26, 59.17, 51.26, 42.14, 36.44.

Treatment of 13c (0.49 g, 0.95 mmol) with LiBr (0.100 g, 1.2 mmol) in EtOAc (60 mL) at 60° C. for 3 h, and chromatography of the product on silica gel, eluting with EtOAc/petroleum ether (from 2:1 to 1:0) gave the dibromide (14c) (0.24 g, 53%). Further elution gave IIb3 (0.20 g, 42%): as yellow foam;

¹H NMR [(CD₃)₂SO] δ 8.77 (m, 1H, CONH), 8.74 (d, J=2.7 Hz, 1H, H-5), 8.36 (d, J=2.7 Hz, 1H, H-3), 4.28 (m, 2H, CH₂OMs), 3.58 (m, 4H), 3.44 (m, 4H), 3.14 (s, 3H, OSO₂CH₃); ¹³C NMR δ 165.33, 145.79, 145.20, 140.87, 135.11, 127.50, 122.19, 67.49, 59.18, 54.21, 50.99, 42.09, 36.44, 29.68. HRMS m/z (M+1)⁺ required for $C_{14}H_{20}{}^{79}BrN_4O_9S$ 499.01344; Found 499.01324.

2-((2-Iodoethyl)-2-{[(2-hydroxyethyl)amino]carbonyl}-4,6-dinitroanilino)ethyl methanesulfonate (IIb4).

Treatment of 13b (6.7 g, 13.0 mmol) with NaI (2.9 g, 20 mmol) in EtOAc (200 mL) at 60° C. for 3 h, and chromatography of the product on silica gel, eluting with EtOAc/petroleum ether (from 2:1 to 1:0) gave 2-[bis(2-iodoethyl)amino]-N-(3-hydroxyethyl)-3,5-dinitrobenzamide (3.3 g, 44%) as a yellow solid:

mp (EtOAc/petroleum ether) 129-131° C.; ¹H NMR [(CD₃)₂SO] δ 8.72 (d, J=2.8 Hz, 1H, H-4), 8.70 (m, 1H, CONH), 8.32 (d, J=2.8 Hz, 1H, H-6), 4.80 (m, 1H), 3.55 (m, 2H), 3.43 (m, 4H), 3.31 (m, 6H); ¹³C NMR δ 165.3, 145.2, 144.7, 141.0, 136.3, 127.3, 122.0, 59.3, 54.7, 42.1, 2.94.

Later eluates gave IIb4 (1.35 g, 19%) as a yellow foam;

¹H NMR [(CD₃)₂SO] δ 8.74 (d, J=2.8 Hz, 1H, H-4), 8.74 (m, 1H, CONH), 8.34 (d, J=2.8 Hz, 1H, H-6), 4.28 (m, 2H), 3.56 (m, 2H), 3.43 (m, 2H), 3.31 (m, 6H), 3.13 (s, 3H); ¹³C NMR δ 165.3, 145.5, 145.2, 140.8, 136.1, 127.4, 122.1, 67.5, 59.2, 55.4, 50.6, 42.1, 36.5, 2.6. HRMS (FAB) Calcd. For $C_{14}H_{20}IN_4O_9S$ [M+H⁺] m/z 546.9996. Found; 546.9997.

2-((2-Bromoethyl)-2-{[(2-hydroxypropyl)amino]carbonyl}-4,6-dinitroanilino)ethyl methanesulfonate (IIb5).

A solution of 12d (1.22 g, 4.0 mmol) in 50 mL of CH₂Cl₂ was cooled in an ice-bath, and 3,4-dihydro-2H-pyran (1.0 mL) and p-toluenesulfonic acid (0.1 g) were added. The reaction mixture was stirred for 2 h, then concentrated under reduced pressure. Chromatography of the residue on silica gel, eluting with EtOAc/petroleum ether (from 1:2 to 2:1), gave 2-chloro-3,5-dinitro-N-[2-(tetrahydro-2H-pyran-2-yloxy)propyl]benzamide (12e) (1.45 g, 94%): as a pale yellow oil;

¹H NMR [(CD₃)₂SO] δ 8.99 (d, J=2.7 Hz, 1H, H-4), 8.81 (m, 1H, CONH), 8.51 (d, J=2.7 Hz, 1H, H-6), 4.57 (m, 1H), 3.72 (m, 2H), 3.46-3.25 (m, 4H), 1.82-1.44 (m, 8H). ¹³C NMR δ 162.7, 148.4, 145.9, 140.3, 128.2, 125.8, 120.5, 98.0, 64.2, 61.3, 36.5, 30.2, 28.9, 24.9, 19.1. HRMS (FAB) Calcd. For $C_{15}H_{19}{}^{35}ClIN_3O_7$ [M+H⁺] m/z 388.0912. Found; 388.0915.

Reaction of 12e (1.45 g, 3.75 mmol) with diethanolamine (1.67 g) as above gave 2-[bis(2-hydroxyethyl)amino]-3,5-dinitro-N-[2-(tetrahydro-2H-pyran-2-yloxy)propyl]benzamide (1.62 g, 95%) as a yellow foam that was used directly;

¹H NMR [(CD₃)₂SO] δ 8.96 (m, 1H, CONH), 8.66 (d, J=2.8 Hz, 1H, H-4), 8.31 (d, J=2.8 Hz, 1H, H-6), 4.95 (m, 2H), 4.56 (m, 1H), 3.79-3.16 (m, 14H), 1.80-1.45 (m, 8H); ¹³C NMR δ 166.2, 148.1, 143.6, 139.3, 133.8, 128.9, 123.8, 98.5, 64.8, 61.7, 58.5, 54.6, 37.3, 30.6, 29.2, 25.4, 19.6. HRMS (FAB) Calcd. For $C_{19}H_{29}N_4O_6$ [M+H⁺] m/z 457.1935. Found; 457.1939.

Reaction of the above diol (1.62 g, 3.55 mmol) with MsCl (2 mL) as above gave 2-[{2-[(methylsulfonyl)oxy]ethyl}-4,6-dinitro-6-({[2-(tetrahydro-2H-pyran-2-yloxy)propyl]-amino}carbonyl)anilino]ethyl methanesulfonate (13e) (2.17 g, 100%): as a yellow foam;

¹H NMR [(CD₃)₂SO] δ 8.71 (d, J=2.8 Hz, 1H), 8.71 (m, 1H), 8.31 (d, J=2.8 Hz, 1H), 4.26 (m, 4H), 3.71-3.37 (m, 10H), 3.13 (s, 6H), 3.10 (m, 2H), 1.82-1.43 (m, 8H); ¹³C NMR δ 165.1, 146.3, 145.4, 140.9, 135.9, 127.4, 122.2, 98.0, 67.2, 64.3, 51.4, 45.7, 36.5, 30.2, 28.7, 24.9, 19.1, 8.5. HRMS (FAB) Calcd. For $C_{21}H_{33}N_4O_{13}S_2$ [M+H⁺] m/z 613.1486. Found; 613.1481.

A solution of 13e (2.95 g, 3.55 mmol) in THF (120 mL) was treated with 1N HCl (80 mL), and the solution was stirred at 20° C. for 1 h, then diluted with water (100 mL), neutralized with satd. NaHCO₃, and extracted with EtOAc (3×80 mL). The combined organic phases were washed with brine and dried, the solvent was evaporated, and the residue was purified by chromatography on silica gel, eluting with EtOAc/MeOH (100:1), to give 2-[{2-[(methylsulfonyl)oxy]ethyl}-4,6-dinitro-6-({[2-hydroxypropyl-amino}carbonyl)anilino] ethyl methanesulfonate (13d) (1.4 g, 75%): as a yellow solid:

mp (EtOAc/petroleum ether) 130-133° C.; ¹H NMR [(CD₃)₂SO] δ 8.74 (d, J=2.8 Hz, 1H), 8.72 (m, 1H), 8.32 (d, J=2.8 Hz, 1H), 4.29 (m, 4H), 3.47 (m, 8H), 3.14 (s, 6H), 1.71 (m, 2H); ¹³C NMR δ 165.2, 146.3, 145.3, 140.8, 135.9, 127.5, 122.3, 67.3, 58.4, 51.4, 36.8, 36.5, 31.7. Anal. ($C_{16}H_{24}N_4O_{12}S_2$) C, H, N.

Treatment of 13d (0.25 g, 0.45 mmol) with LiBr (53 mg, 0.7 mmol) in EtOAc (50 mL) at 60° C. for 3 h, and chromatography of the product on silica gel, eluting with EtOAc/petroleum ether (from 2:1 to 1:0) gave IIb5 (0.16 g, 66%): as yellow foam;

¹H NMR [(CD₃)₂SO] δ 8.74 (d, J=2.8 Hz, 1H), 8.73 (m, 1H), 8.31 (d, J=2.8 Hz, 1H), 4.28 (m, 2H), 3.65-3.44 (m, 10H), 3.13 (s, 3H), 1.70 (m, 2H); ¹³C NMR δ 165.1, 145.7, 145.4, 141.0, 136.2, 127.3, 122.1, 67.5, 58.4, 51.1, 36.7, 36.5, 31.7, 29.6. HRMS (FAB) Calcd. For $C_{15}H_{22}{}^{79}BrN_4O_9S$ [M+H⁺] m/z 513.0291. Found; 513.0281.

2-((2-Bromoethyl)-2-{[(2,3-dihydroxypropyl)amino]carbonyl}-4,6-dinitroanilino)ethyl methanesulfonate (IIb6).

A solution of 2-(2-({[(2,2-dimethyl-1,3-dioxolan-4-yl)methyl]amino}carbonyl){2-[(methylsulfonyl)oxy]ethyl}-4, 6-dinitroanilino)ethyl methanesulfonate (13g) [Palmer et al., *J. Med. Chem.* 1997, 40, 1272] (5.0 mmol) in MeOH (200 mL) was treated with p-toluenesulfonic acid (0.2 g) at room temperature for 4 h. Most of the MeOH was then evaporated, and the residue was taken up in EtOAc (200 mL), washed with satd. NaHCO$_3$ and brine, dried and concentrated. Chromatography of the product on silica gel, eluting with EtOAc/MeOH (20:1), gave 2-(2-{[(2,3-dihydroxypropyl)amino]carbonyl}{2-[(methylsulfonyl)oxy]ethyl}-4,6-dinitroanilino)ethyl methanesulfonate (13f) (2.0 g, 73%): as yellow foam;

$^1$H NMR [(CD$_3$)$_2$SO] δ 8.77 (m, 1H, CONH), 8.74 (d, J=3.0 Hz, 1H, H-5), 8.37 (d, J=3.0 Hz, 1H, H-3), 4.30 (m, 4H, 2×CH$_2$OMs), 3.66 (m, 1H), 3.48-3.30 (m, 8H), 3.14 (s, 6H, 2×OSO$_2$CH$_3$); $^{13}$C NMR δ 165.42, 146.24, 145.09, 140.60, 135.77, 127.67, 122.26, 69.77, 67.29, 63.87, 51.29, 42.98, 36.44. HRMS m/z (M+1)$^+$ required for C$_{16}$H$_{25}$N$_4$O$_{13}$S$_2$ 545.08596; Found 545.08680.

Treatment of 13f (1.50 g, 2.75 mmol) with LiBr (0.21 g, 2.0 mmol) in EtOAc (60 mL) at 60° C. for 3 h, followed by chromatography on silica gel and elution with EtOAc/MeOH 20:1), gave the dibromide 14f (0.5 g, 35%) as a yellow foam and then IIb6 (0.62 g, 34%): yellow solid;

$^1$H NMR [(CD$_3$)$_2$SO] δ 8.74 (d, J=2.8 Hz, 1H, H-5), 8.71 (m, 1H, CONH), 8.36 (d, J=2.8 Hz, 1H, H-3), 4.28 (m, 2H, CH$_2$OMs), 3.69-3.30 (m, 11H), 3.14 (s, 3H); $^{13}$C NMR δ 165.52, 145.87, 145.30, 140.93, 136.20, 127.64, 122.23, 68.89, 67.62, 63.93, 54.35, 51.08, 43.04, 36.52, 29.80. Anal. Calcd for C$_{15}$H$_{21}$BrN$_4$O$_{10}$S: C, 34.1; H, 4.0; N, 10.6; Br, 15.0. Found: C, 34.0; H, 4.0; N, 10.5; Br, 15.2%. Further elution gave starting material 8e (0.28, 19%).

2-[(2-Bromoethyl)-2-({[3-(4-morpholinyl)propyl] amino}carbonyl)-4,6-dinitroanilino]ethyl methanesulfonate (IIb7).

2-Chloro-N-[3-(4-morpholinyl)propyl]-3,5-dinitrobenzamide (12h) (0.5 g, 1.34 mmol) was reacted with diethanolamine (0.5 g) in p-dioxane (10 mL) at room temperature for 3 h. The reaction mixture was poured into brine, extracted with EtOAc (3×70 mL), and the combined organic phases were dried and concentrated under reduced pressure to give crude 2-[bis(2-hydroxyethyl)amino]-N-[3-(4-morpholinyl)propyl]-3,5-dinitrobenzamide. This was dissolved in CH$_2$Cl$_2$ (100 mL), cooled in an ice-bath, and treated with Et$_3$N (1.5 mL) followed by MsCl (0.7 mL) in one portion. After stirring for 10 min, sat. NaHCO$_3$ (100 mL) was added and the mixture was stirred for a further 30 min, then the aqueous phase was extracted with CH$_2$Cl$_3$ (2×70 mL). The combined organic phases were dried and evaporated under reduced pressure. The residue was purified by column chromatography, eluting with EtOAc/MeOH (20:1 to 9:0) to give yield 2-[{2-[(methylsulfonyl)oxy]ethyl}-2-({[3-(4-morpholinyl)propyl] amino}carbonyl)-4,6-dinitroanilino]ethyl methanesulfonate (13h) (0.75 g, 93%) as a foam;

$^1$H NMR [(CD$_3$)$_2$SO] δ 8.77 (m, 1H, CONH), 8.74 (d, J=2.7 Hz, 1H, H-5), 8.20 (d, J=2.7 Hz, 1H, H-3), 4.28 (m, 4H, 2×CH$_2$OMs), 3.56 (m, 5H), 3.44 (m, 5H), 3.15 (s, 6H), 2.35 (m, 6H), 1.71 (m, 2H).

A solution of 13h (0.70 g, 1.17 mmol) in EtOAc (100 mL) was treated with LiBr (118 mg, 1.36 mmol) at 60° C. for 2 h. Volatiles were removed under reduced pressure, and the residue was adsorbed directly onto silica gel and chromatographed. Elution with EtOAc/MeOH (from 20:1 to 10:1) gave 2-[bis(2-bromoethyl)amino]-N-[3-(4-morpholinyl)propyl]-3,5-dinitrobenzamide (14h) 228 mg (34%) as a yellow oil;

$^1$H NMR [(CD$_3$)$_2$SO] δ 8.77 (m, 1H, CONH), 8.76 (d, J=2.8 Hz, 1H, H-5), 8.30 (d, J=2.8 Hz, 1H, H-3), 3.58-3.42 (m, 14H), 2.36 (m, 6H), 1.70 (m, 2H); $^{13}$C NMR δ 165.08, 145.57, 145.27, 141.19, 136.40, 127.27, 122.10, 66.08, 59.66, 55.64, 53.19, 37.61, 25.39, 13.99. HRMS m/z (M+1)$^+$ required for C$_{18}$H$_{25}$$^{79}$Br$_2$N$_5$O$_6$: 566.0250. Found; 566.0241. Later eluates gave IIb7 (300 mg, 44%); as yellow foam;

$^1$H NMR [(CD$_3$)$_2$SO] δ 8.77 (m, 1H, CONH), 8.75 (d, J=2.6 Hz, 1H, H-4), 8.31 (d, J=2.6 Hz, 1H, H-6), 4.28 (m, 2H, CH$_2$OMs), 3.56 (m, 7H), 3.44 (m, 5H), 3.14 (s, 3H), 2.35 (m, 6H), 1.71 (m, 2H); $^{13}$C NMR δ 165.07, 145.79, 145.31, 140.92, 136.04, 127.36, 122.21, 67.50, 66.09, 59.64, 55.68, 53.21, 51.10, 37.63, 36.45, 25.41, 14.00. HRMS m/z (M+1)$^+$ required for C$_{19}$H$_{29}$$^{79}$BrN$_5$O$_9$S 582.08519. Found 582.08694; together with starting material 13h (117 mg, 18%).

Methyl 3-{[2-((2-chloroethyl){2-[(methylsulfonyl)oxy] ethyl}amino)-3,5-dinitrobenzoyl]amino}propanoate (IIb8).

Methyl alanine hydrochloride (2.55 g, 18.3 mmol) was dissolved in water (12 mL), and the solution was diluted with Me$_2$CO (20 mL) and Et$_2$O (50 mL). This was then poured into a solution of crude 2-chloro-3,5-dinitrobenzoyl chloride [prepared from 2-chloro-3,5-dinitrobenzoic acid 11 (5.0 g, 18.3 mmol) with SOCl$_2$] in Me$_2$CO (50 mL) while cooling in an ice-bath. The mixture was stirred for 30 min, then poured into water and extracted with EtOAc. The organic phase was washed with satd. NaHCO$_3$ and brine, dried, and concentrated to give methyl 3-[(2-chloro-3,5-dinitrobenzoyl)amino] propanoate (12i) (4.45 g, 73.3%):

mp (EtOAc/petroleum ether) 128-130° C.; $^1$H NMR [(CD$_3$)$_2$SO] δ 8.99 (d, J=2.7 Hz, 1H, H-4), 8.96 (m, 1H, CONH), 8.51 (d, J=2.7 Hz, 1H, H-6), 3.63 (s, 3H, CO$_2$CH$_3$), 3.50 (m, 2H, CONHCH$_2$), 2.64 (m, 2H, CH$_2$CO$_2$). The product was used without further purification.

A mixture of 12i (2.5 g, 7.6 mmol) and diethanolamine (2.0 g) in p-dioxane (30 mL) was kept at room temperature for 3 h, then poured into brine and extracted with EtOAc (3×70 mL). The combined organic phases were dried and evaporated under reduced pressure. The residue was dissolved in CH$_2$Cl$_2$ (15 mL), cooled in an ice-bath, and treated with Et$_3$N (8 mL) and MsCl (4 mL). After stirring for 10 min, satd. NaHCO$_3$ (100 mL) was added, and following a further 30 min of stirring the aqueous phase was extracted with CH$_2$Cl$_3$ (2×70 mL). The combined organic phases were dried and then evaporated under reduced pressure, and the residue was then purified by column chromatography on silica gel. Elution with EtOAc/petroleum ether (1:1 to 1:0) gave IIb8 (0.2 g, 5%): as yellow oil;

$^1$H NMR [(CD$_3$)$_2$SO] δ 8.88 (m, 1H, CONH), 8.74 (d, J=2.7 Hz, 1H, H-4), 8.31 (d, J=2.7 Hz, 1H, H-6), 4.29 (m, 2H, CH$_2$OMs), 3.71 (m, 2 H, CH$_2$Cl), 3.63 (s, 3H, CO$_2$CH$_3$), 3.54-3.36 (m, 6H), 3.14 (s, 3H, OSO$_2$CH$_3$), 2.65 (m, 2H, CH$_2$CO$_2$); $^{13}$C NMR δ 171.68, 165.34, 146.14, 145.17, 140.74, 135.59, 127.58, 122.42, 67.47, 54.22, 51.45, 51.22, 41.37, 36.48, 35.44, 32.95. HRMS m/z (M+1)$^+$ required for C$_{16}$H$_{22}$$^{35}$ClN$_4$O$_{10}$S; 497.0745. Found; 497.0748.

Further elution gave methyl 3-{[2-bis{2-[(methylsulfonyl) oxy]ethyl}amino)-3,5-dinitrobenzoyl]amino}propanoate (13i) (2.6 g, 62%): as yellow oil;

$^1$H NMR [(CD$_3$)$_2$SO] δ 8.90 (m, 1H, CONH), 8.74 (d, J=2.7 Hz, 1H, H-4), 8.32 (d, J=2.7 Hz, 1H, H-6), 4.30 (m, 4H, 2×CH$_2$OMs), 3.63 (s, 3H, CO$_2$CH$_3$), 3.52 (m, 2H, CONHCH$_2$), 3.44 (m, 4H, 2×CH$_2$N), 3.14 (s, 6H, 2×OSO$_2$CH$_3$), 2.65 (m, 2H, CH$_2$CO$_2$); $^{13}$C NMR δ 171.66, 165.28, 146.36, 144.98, 140.52, 135.23, 127.64, 122.50, 67.20, 51.40, 51.25, 36.44, 35.45, 32.91. HRMS m/z (M+1)$^+$ required for C$_{17}$H$_{25}$N$_4$O$_{13}$S$_2$: 557.0860. Found: 557.0853.

In an alternative preparation of IIb8, a solution of 13i (0.417 g, 0.75 mmol) in DMF (10 mL) was treated with LiCl (0.038 g, 1.00 mmol) at 60° C. for 2 h, and then cooled and poured into dilute HCl and extracted with EtOAc (3×80 mL). Workup and chromatography of the product on silica gel, eluting with EtOAc/petroleum ether from 1:1 to 2:1, gave methyl 3-({2-[bis(2-chloroethyl)amino]-3,5-dinitrobenzoyl}amino)propanoate (15i) (0.16 g, 51%): as yellow oil;

$^1$H NMR [(CD$_3$)$_2$SO] δ 8.85 (m, 1H, CONH), 8.74 (d, J=2.7 Hz, 1H, H-4), 8.29 (d, J=2.7 Hz, 1H, H-6), 3.68 (m, 4H, 2×CH$_2$Cl), 3.63 (s, 3H, CO$_2$CH$_3$), 3.50 (m, 2H, CONHCH$_2$), 3.41 (m, 4H, N(CH$_2$)$_2$), 2.64 (m, 2H, CH$_2$CO$_2$); $^{13}$C NMR δ 171.59, 165.28, 145.81, 145.31, 140.89, 135.89, 127.45, 122.26, 54.08, 51.40, 41.51, 35.35, 32.92. Further elution then gave IIb8 (0.124 g, 33%), identical with the sample prepared above.

Methyl 3-{[2-((2-bromoethyl){2-[(methylsulfonyl)oxy]ethyl}amino)-3,5-dinitrobenzoyl]amino}propanoate (IIb9).

Treatment of 13i (2.04 g, 3.67 mmol) with LiBr (0.318 g, 3.67 mmol) in EtOAc (100 mL) at 60° C. for 3 h, followed by chromatography on silica gel and elution with EtOAc/petroleum ether from 1:1 to 1:0) gave methyl 3-({2-[bis(2-bromoethyl)amino]-3,5-dinitrobenzoyl}amino)propanoate (14i) (0.55 g, 29%): as yellow foam;

$^1$H NMR [(CD$_3$)$_2$SO] δ 8.86 (m, 1H, CONH), 8.74 (d, J=2.7 Hz, 1H, H-4), 8.29 (d, J=2.7 Hz, 1H, H-6), 3.63 (s, 3H, CO$_2$CH$_3$), 3.60-3.43 (m, 10H), 2.64 (m, 2H, CH$_2$CO$_2$); $^{13}$C NMR δ 171.60, 165.28, 145.39, 145.36, 141.07, 136.05, 127.44, 122.25, 53.97, 51.44, 35.35, 32.95, 29.96. HRMS m/z (M+1)$^+$ required for C$_{15}$H$_{19}$$^{79}$Br$_2$N$_4$O$_7$: 524.9621. Found; 524.9616.

Further elution gave IIb9 (0.96 g, 48%): as yellow foam;

$^1$H NMR [(CD$_3$)$_2$SO] δ 8.89 (m, 1H, CONH), 8.74 (d, J=2.7 Hz, 1H, H-4), 8.31 (d, J=2.7 Hz, 1H, H-6), 4.28 (m, 2H, CH$_2$OMs), 3.63 (s, 3H, CO$_2$CH$_3$), 3.60-3.43 (m, 8H), 3.14 (s, 3H, OSO$_2$CH$_3$), 2.65 (m, 2H, CH$_2$CO$_2$); $^{13}$C NMR δ 171.63, 165.28, 145.87, 145.19, 140.81, 135.65, 127.54, 122.37, 67.47, 54.25, 51.42, 51.02, 36.45, 35.40, 32.93, 29.69. HRMS m/z (M+1)$^+$ required for C$_{16}$H$_{22}$$^{79}$BrN$_4$O$_{10}$S: 541.0240. Found; 541.0228, followed by starting material 13g (0.45 g, 22%).

Example C

Preparation of Analogues of Class IIc by the Method Outlined in Scheme 3

2-[3-(Aminocarbonyl)(2-chloroethyl)-2,4-dinitroanilino]ethyl methanesulfonate (IIc1).

A solution of methyl 3-[bis(2-hydroxyethyl)amino]-2,6-dinitrobenzoate [Palmer et al., *J. Med. Chem.* 1996, 39, 2518] (7.24 g, 22 mmol) in CH$_2$Cl$_2$ (120 mL) was cooled in an ice-bath and Et$_3$N (15 mL) and MsCl (8 mL) were added in one portion. After stirred for 10 min, satd. NaHCO$_3$ (100 mL) was added, and after a further 30 min the aqueous phase was extracted with CH$_2$Cl$_2$ (2×70 mL), the combined organic phase were dried, concentrated under reduced pressure, and the residue was purified by column chromatography on silica gel. Elution with EtOAc/petroleum ether (1:1 to 1:0), gave crude methyl 3-(bis{2-[(methylsulfonyl)oxy]ethyl}amino)-2,6-dinitrobenzoate (16) (10.67 g, 100%) as yellow oil;

$^1$H NMR [(CD$_3$)$_2$SO] δ 8.32 (d, J=9.6 Hz, 1H, H-5), 7.75 (d, J=9.6 Hz, 1H, H-4), 4.32 (m, 4H), 3.88 (s, 3H), 3.67 (m, 4H), 3.14 (m, 6H); $^{13}$C NMR δ 163.02, 147.59, 138.40, 136.46, 128.33, 125.83, 123.96, 66.73, 54.00, 50.24, 45.58, 36.58.

Hydrolysis of 16 (10.6 g, 21.9 mmol) with 3 N KOH (40 mL) in dioxane (200 mL) at room temperature for 15 min, followed by acidification with 1 N HCl and extraction with EtOAc, gave a quantitative yield of crude 3-(bis{2-[(methylsulfonyl)oxy]ethyl}amino)-2,6-dinitrobenzoic acid (17):

mp 200-210° C.; HRMS: C$_{13}$H18N$_3$O$_{12}$S$_2$ requires m/z 472.0332. Found: 472.033, that was used without purification. The acid chloride (SOCl$_2$/cat. DMF) from 17 (3.2 g, 6.8 mmol) was dissolved in Me$_2$CO (30 mL), cooled in an ice-bath and treated with concentrated NH$_4$OH (10 mL). After stirring for 10 min. the reaction mixture was acidified to pH 2-3 with 1 N HCl, then most of the solvent was evaporated and the residue was partitioned between EtOAc and water. The aqueous layer was extracted with EtOAc (2×80 mL) and the combined organic extracts were dried and evaporated under reduced pressure. The residue was adsorbed directly onto silica gel and chromatographed. Elution with EtOAc/petroleum ether (from 1:1 to 1:0) gave IIc1 (0.145 g, 5.2%:

mp (EtOAc) 134-136° C.; $^1$H NMR [(CD$_3$)$_2$SO] δ 8.25 (d, J=9.3 Hz, 1H, H-5), 8.23 (s, 1H, NH), 7.89 (s, 1H, NH), 7.64 (d, J=9.3 Hz, 1H, H-6), 4.27 (m, 2H, CH$_2$OMs), 3.73 (m, 2H), 3.66 (m, 2H), 3.59 (m, 2H), 3.15 (s, 3H); $^{13}$C NMR δ 163.06, 146.40, 140.52, 137.65, 129.42, 127.51, 122.89, 66.83, 52.93, 50.16, 41.45, 36.57. Anal. Calcd. For C$_{12}$H$_{15}$ClN$_4$O$_8$S: C, 35.1; H, 3.7; N, 13.6; Cl, 8.6. Found: C, 35.5; H, 3.7; N, 13.6; Cl, 8.6%.

Elution of the column with EtOAc/MeOH (50:1) gave 2-(3-(aminocarbonyl){2-[(methylsulfonyl)oxy]ethyl}-2,6-dinitroanilino)ethyl methanesulfonate (18a) (1.1 g, 34%):

mp (EtOAc/MeOH/petroleum ether) 160-162° C.; $^1$H NMR [(CD$_3$)$_2$SO] δ 8.26 (d, J=9.3 Hz, 1H, H-5), 8.23 (s, 1H, NH), 7.89 (s, 1H, NH), 7.66 (d, J=9.3 Hz, 1H, H-6), 4.27 (m, 4H, 2×-CH$_2$OMs), 3.63 (m, 4H, 2×-CH$_2$N), 3.15 (s, 6H, 2×CH$_3$SO$_3$—); $^{13}$C NMR δ 163.00, 146.51, 140.98, 137.99, 129.30, 127.47, 123.40, 66.74, 50.44, 36.56. Anal. Calcd. For C$_{13}$H$_{18}$N$_4$O$_{11}$S$_2$: C, 33.2; H, 3.9; N, 11.9. Found: C, 33.5; H, 3.8; N, 11.9%.

2-[3-(Aminocarbonyl)(2-bromoethyl)-2,6-dinitroanilino]ethyl methanesulfonate (IIc2).

LiBr (117 mg, 1.34 mmol) was added in one portion to a solution of 18a (0.474 g, 1.0 mmol) in Me$_2$CO/EtOAc (1:1, 100 mL), and the reaction mixture was heated to 60° C. for 2 h. Volatiles were removed under reduced pressure, and the residue was adsorbed directly onto silica gel and chromatographed. Elution with EtOAc/petroleum ether (1:1) gave 3-[bis(2-bromoethyl)amino]-2,6-dinitrobenzamide (19a) (95 mg, 21%): as a yellow oil;

$^1$H NMR [(CD$_3$)$_2$SO] δ 8.25 (d, J=9.5 Hz, 1H, H-5), 8.22 (s, 1H, NH), 7.88 (s, 1H, NH), 7.63 (d, J=9.5 Hz, 1H, H-4), 3.68 (m, 4H), 3.58 (m, 4H (Lit. [Palmer et al., J. Med. Chem., 1996, 39, 2518-2528].

Further elution with EtOAc/petroleum ether (3:1) gave IIc2 (208 mg, 46%):

mp (EtOAc/petroleum ether) 143-145° C.; $^1$H NMR [(CD$_3$)$_2$SO] δ 8.25 (d, J=9.3 Hz, 1H, H-5), 8.23 (s, 1H, NH), 7.89 (s, 1H, NH), 7.64 (d, J=9.3 Hz, 1H, H-6), 4.28 (m, 2H, CH$_2$OMs), 3.67 (m, 4H), 3.57 (m, 2H), 3.16 (s, 3H); $^{13}$C NMR δ 163.05, 146.17, 140.49, 137.68, 129.42, 127.53, 122.89, 66.85, 52.92, 50.04, 36.57, 29.95. Anal. Calcd. For C$_{12}$H$_{15}$BrN$_4$O$_8$S: C, 31.7; H, 3.3; N, 12.3; Br, 17.4. Found: C, 31.9; H, 3.3; N, 12.2; Br, 17.5%.

Later eluates gave starting material 18a (150 mg).

2-((2-Bromoethyl)-3-{[(2-hydroxyethyl)amino]carbonyl}-2,6-dinitroanilino)ethyl methanesulfonate (IIc3).

Treatment of 3-(3-{[(2-hydroxyethyl)amino]carbonyl}{3-[(methylsulfonyl)oxy]butyl}-2,4-dinitroanilino)-1-methylpropyl methanesulfonate (18b)] (310 mg, 0.6 mmol) in EtOAc (50 mL) with LiBr (78 mg, 0.9 mmol), followed by chromatography on silica gel and elution with EtOAc/petroleum ether (from 1:1 to 1:0) gave 3-[bis(2-bromoethyl) amino]-N-(2-hydroxyethyl)-2,6-dinitrobenzamide (19b) (70 mg, 25%) as a foam;

$^1$H NMR [(CD$_3$)$_2$SO] δ 8.80 (m, 1H, CONH), 8.24 (d, J=9.4 Hz, 1H), 7.63 (d, J=9.4 Hz, 1H), 4.66 (m, 1H), 3.70 (m, 4H), 3.60 (m, 4H), 3.45 (m, 2H), 3.22 (in, 2H); $^{13}$C NMR δ 161.4, 145.8, 140.2, 137.5, 129.2, 127.6, 122.6, 59.0, 52.6, 41.7, 30.0. HRMS (FAB) Calcd. For C$_{13}$H$_{17}$$^{79}$Br$_2$N$_4$O$_6$[M+H$^+$] m/z 482.9515. Found; 482.9508.

Further elution with EtOAc/MeOH (50:2) gave IIc3 (118 mg, 39%):

mp. 94-97° C.; $^1$H NMR [(CD$_3$)$_2$SO] δ 8.80 (m, 1H, CONH), 8.25 (d, J=9.4 Hz, 1H), 7.64 (d, J=9.4 Hz, 1H), 4.67 (m, 1H), 4.27 (m, 2H), 3.63 (m, 4H), 3.57 (m, 2H), 3.45 (m, 2H), 3.26 (m, 2H), 3.15 (s, 3H); $^{13}$C NMR δ 161.4, 146.2, 140.5, 137.7, 129.2, 127.5, 122.9, 66.8, 59.0, 50.0, 41.7, 36.6, 29.9. Anal. (C$_{14}$H$_{19}$BrN$_4$O$_9$S) C, H, N.

2-((2-Chloroethyl)-3-{[(3-hydroxypropyl)amino]carbonyl}-2,4-dinitroanilino)ethyl methanesulfonate (IIc4).

Reaction of the acid chloride of 17 with 3-aminopropanol in Me$_2$CO at 0° C. as described above, followed by chromatography of the product on silica gel and elution with EtOAc/petroleum ether (1:1), gave IIc4 (292 mg, 12%):

mp (EtOAc/petroleum ether) 104-109° C.; $^1$H NMR [(CD$_3$)$_2$SO] δ 8.75 (t, J=5.8 Hz, 1H, CONH, 8.24 (d, J=9.4 Hz, 1H, H-5), 7.64 (d, J=9.4 Hz, 1H, H-6), 4.44 (m, 1H, CHOH), 4.26 (m, 2H), 3.72 (m, 2H), 3.65 (m, 2H), 3.59 (m, 2H), 3.43 (m, 2H), 3.20 (m, 2H), 3.15 (s, 3H), 1.60 (m, 2H); $^{13}$C NMR δ 161.09, 146.42, 140.49, 137.65, 129.23, 127.58, 122.91, 66.82, 58.22, 52.88, 50.11, 41.44, 36.57, 36.37, 31.57. Anal. Calcd. For C$_{15}$H$_{21}$ClN$_4$O$_9$S: C, 38.5; H, 4.5; N, 12.0; Cl, 7.5. Found: C, 38.8; H, 4.8; N, 11.5; Cl, 7.0%.

Further elution with EtOAc gave 2-(3-{[(3-hydroxypropyl)amino]carbonyl}{2-[(methylsulfonyl)oxy]ethyl}-2,4-dinitroanilino)ethyl methanesulfonate (18e) (1.1 g, 41%):

mp (EtOAc/MeOH/petroleum ether) 160-162° C.; $^1$H NMR [(CD$_3$)$_2$SO] δ 8.77 (t, J=5.8 Hz, 1H, CONH), 8.26 (d, J=9.4 Hz, 1H, H-5), 7.66 (d, J=9.4 Hz, 1H, H-6), 4.43 (m, 1H, CHOH), 4.27 (m, 4H, 2×CH$_2$OMs), 3.63 (m, 4H, 2×CH$_2$N), 3.43 (m, 2H), 3.20 (m, 2H), 3.15 (s, 6H, 2×CH$_3$SO$_3$), 1.60 (m, 2H); $^{13}$C NMR δ 161.03, 146.52, 140.95, 138.00, 129.12, 127.54, 123.42, 66.72, 58.22, 50.39, 36.55, 36.37, 31.57. Anal. Calcd. For C$_{16}$H$_{24}$N$_4$O$_{12}$S$_2$: C, 36.4; H, 4.6; N, 10.6. Found: C, 36.6; H, 4.5; N, 10.6%.

2-((2-Bromoethyl)-3-{[(3-hydroxypropyl)amino]carbonyl}-2,6-dinitroanilino)ethyl methanesulfonate (IIc5).

Treatment of 18c (716 mg, 1.36 mmol) in EtOAc (200 mL) with LiBr ((175 mg, 2.0 mmol) as above, followed by chromatography on silica gel and elution with EtOAc/etroleum ether (from 1:1 to 1:0) gave 3-[bis(2-bromoethyl)amino]-N-(3-hydroxypropyl)-2,6-dinitrobenzamide (19c) (289 mg, 42%) as a foam;

$^1$H NMR [(CD$_3$)$_2$SO] δ 8.75 (t, J=5.8 Hz, 1H, CONH), 8.23 (d, J=9.4 Hz, 1H, H-5), 7.62 (d, J=9.4 Hz, 1H, H-4), 4.47 (m, 1H, CHOH), 3.68 (m, 4H), 3.57 (m, 4H), 3.43 (m, 2H), 3.20 (m, 2H), 1.60 (m, 2H); $^{13}$C NMR δ 161.20, 146.90, 140.20, 137.53, 129.36, 127.69, 122.56, 58.29, 52.64, 36.42, 31.61, 30.13. HRMS m/z (M+1)$^+$ required for C$_{14}$H$_{19}$$^{79}$Br$_2$N$_4$O$_6$: 496.9671. Found: 496.9667.

Further elution with EtOAc/MeOH (50:2) gave IIc5 (270 mg, 39%):

mp. 115-117° C.; $^1$H NMR [(CD$_3$)$_2$SO] δ 8.75 (t, J=5.8 Hz, 1H, CONH, 8.24 (d, J=9.4 Hz, 1H, H-5), 7.64 (d, J=9.4 Hz, 1H, H-6), 4.43 (m, 1H, CHOH), 4.27 (m, 2H, CH$_2$OMs), 3.66 (m, 4H, 2×CH$_2$N), 3.59 (m, 2H), 3.44 (m, 2H), 3.22 (m, 2H), 3.15 (s, 3H, CH$_3$SO$_3$), 1.60 (m, 2H); $^{13}$C NMR δ 161.08, 146.19, 140.47, 137.69, 129.24, 127.59, 122.91, 66.83, 58.22, 52.87, 50.00, 36.57, 36.37, 31.58, 29.95. Anal. Calcd. For C$_{15}$H$_{21}$BrN$_4$O$_9$S: C, 35.2; H, 4.1; N, 10.9; Br, 15.4. Found: C, 35.4; H, 3.9; N, 11.0; Br, 16.3%.

2-((2-Bromoethyl)-3-{[(4-hydroxybutyl)amino] carbonyl}-2,6-dinitroanilino)ethyl methanesulfonate (IIc6).

Treatment of 3-(3-{[(4-hydroxybutyl)amino]carbonyl}{3-[(methylsulfonyl)oxy]butyl}-2,4-dinitroanilino)-1-methylpropyl methanesulfonate (18d) (500 mg, 0.92 mmol) in EtOAc (100 mL) with LiBr (110 mg, 1.4 mmol), followed by chromatography on silica gel and elution with EtOAc/petroleum ether (from 1:1 to 1:0) gave 3-[bis(2-bromoethyl)amino]-N-(4-hydroxybutyl)-2,6-dinitrobenzamide (19d) (100 mg, 21%) as a foam; 1H NMR [(CD$_3$)$_2$SO] δ 8.73 (m, 1H, CONH), 8.25 (d, J=9.4 Hz, 1H), 7.63 (d, J=9.4 Hz, 1H), 4.38 (m, 1H), 3.69 (m, 4H), 3.57 (m, 4H), 3.40 (m, 2H), 3.14 (m, 2H), 1.47 (m, 4H); $^{13}$C NMR δ 161.0, 145.8, 140.2, 137.6, 129.3, 127.6, 122.6, 60.2, 52.6, 30.0, 29.6, 24.8. HRMS (FAB) Calcd. For C$_{15}$H$_{20}$$^{79}$Br$_2$N$_4$O$_6$ [M+H$^+$] m/z 510.9828. Found; 510.9819.

Further elution with EtOAc/MeOH (50:2) gave IIc6 (117 mg, 30%):

mp. 114-117° C.; $^1$H NMR [(CD$_3$)$_2$SO] δ 8.74 (m, 1H, CONH), 8.25 (d, J=9.4 Hz, 1H), 7.65 (d, J=9.4 Hz, 1H), 4.37 (m, 1H), 4.27 (m, 2H), 3.65 (m, 4H), 3.57 (m, 2H), 3.35 (m, 2H), 3.16 (m, 2H), 3.15 (s, 3H), 1.47 (m, 4H); $^{13}$C NMR δ 160.0, 146.1, 140.6, 137.8, 129.2, 127.5, 122.9, 66.8, 60.2, 52.9, 50.0, 36.6, 29.9, 29.6, 24.9. Anal. (C$_{16}$H$_{23}$BrN$_4$O$_9$S) C, H, N.

2-((2-Chloroethyl)-3-{[(2,3-dihydroxypropyl)amino]carbonyl}-2,4-dinitroanilino)ethyl methanesulfonate (IIc7).

Reaction of the acid chloride of 17 (2.4 g, 5.1 mmol) with 3-amino-1,2-propanediol Me$_2$CO at 0° C. as described above, followed by chromatography of the product on silica gel and elution with EtOAc, gave IIc7 (240 mg, 10%):

mp (EtOAc) 100-105° C.; $^1$H NMR [(CD$_3$)$_2$SO] δ 8.77 (t, J=5.8 Hz, 1H, CONH), 8.24 (d, J=9.4 Hz, 1H, H-5), 7.64 (d, J=9.4 Hz, 1H, H-6), 4.72 (d, J=4.9, 1H, CHOH), 4.52 (t, J=5.7, 1H, CH$_2$OH), 4.27 (m, 2H, CH$_2$OMs), 3.74-3.50 (m, 10H), 3.15 (s, 3H, CH$_3$SO$_3$), 3.04 (m, 1H); $^{13}$C NMR δ 161.48, 146.38, 140.55, 137.73, 129.28, 127.51, 122.88, 69.89, 66.83, 63.57, 52.95, 50.17, 42.55, 41.43, 36.58. Anal. Calcd. For C$_{15}$H$_{21}$ClN$_4$O$_{10}$S: C, 37.2; H, 4.4; N, 11.6; Cl, 7.2. Found: C, 38.0; H, 4.5; N, 11.1; Cl, 7.2%.

Further elution with EtOAc/MeOH (50:1) gave 2-(3-{[(2,3-dihydroxypropyl)amino]carbonyl}{2-[(methylsulfonyl)oxy]ethyl}-2,4-dinitroanilino)ethyl methanesulfonate (18e) (480 mg, 51%):

mp (MeOH/EtOAc) 60-63° C.; $^1$H NMR [(CD$_3$)$_2$SO] δ 8.78 (t, J=5.8 Hz, 1H, CONH), 8.24 (d, J=9.4 Hz, 1H, H-5), 7.66 (d, J=9.4 Hz, 1H, H-6), 4.72 (d, J=4.9, 1H, CHOH), 4.52 (t, J=5.7, 1H, CH$_2$OH), 4.27 (m, 4H, 2×CH$_2$OMs), 3.63 (m, 4H), 3.52-3.30 (m, 5H), 3.15 (s, 3H, 2×CH$_3$SO$_3$), 3.06 (m, 1H); $^{13}$C NMR δ 161.43, 146.49, 141.01, 138.07, 129.15, 127.47, 123.36, 69.89, 66.73, 63.67, 50.44, 42.55, 36.56. Anal. Calcd. For C$_{16}$H$_{24}$N$_4$O$_{13}$S$_2$: C, 35.3; H, 4.5; N, 10.3. Found: C, 35.8; H, 4.5; N, 10.5%.

2-((2-Bromoethyl)-3-{[(2,3-dihydroxypropyl)amino]carbonyl}-2,4-dinitroanilino)ethyl methanesulfonate (IIc8).

Treatment of 18e (0.92 g, 1.7 mmol) in EtOAc (200 mL) with LiBr (170 mg, 1.95 mmol) as above, followed by chromatography on silica gel and elution with EtOAc/MeOH (50:1), gave 3-[bis(2-bromoethyl)amino]-N-(2,3-dihydroxypropyl)-2,4-dinitrobenzamide (19e) (155 mg, 18%) as yellow oil;

$^1$H NMR [(CD$_3$)$_2$SO] δ 8.76 (t, J=5.8 Hz, 1H, CONH), 8.23 (d, J=9.5 Hz, 1H, H-5), 7.63 (d, J=9.5 Hz, 1H, H-6), 4.72 (d, J=5.1 Hz, 1H, CHOH), 4.52 (t, J=5.7 Hz, 1H, CH$_2$OH), 3.70-3.50 (m, 11H), 3.04 (m, 1H). HRMS m/z (M+1)$^+$ required for C$_{14}$H$_{19}$$^{79}$Br$_2$N$_4$O$_7$: 512.9621. Found; 512.9603.

Further elution gave IIc8 (278 mg, 31%):

mp (EtOAc) 108-110° C.; $^1$H NMR [(CD$_3$)$_2$SO] δ 8.77 (t, J=5.8 Hz, 1H, CONH), 8.24 (d, J=9.4 Hz, 1H, H-5), 7.64 (d, J=9.4 Hz, 1H, H-6), 4.72 (d, J=4.9, 1H, CHOH), 4.52 (t, J=5.7, 1H, CH$_2$OH), 4.27 (m, 2H, CH$_2$OMs), 3.70-3.50 (m, 10H), 3.15 (s, 3H, CH$_3$SO$_3$), 3.06 (m, 1H); $^{13}$C NMR δ 161.47, 146.16, 140.52, 137.77, 129.28, 127.53, 122.88, 69.89, 66.84, 63.57, 52.94, 50.05, 42.55, 36.58, 29.94. Anal. Calcd. For C$_{15}$H$_{21}$BrN$_4$O$_{10}$S: C, 34.1; H, 4.0; N, 10.6; Br, 15.0. Found: C, 34.3; H, 4.1; N, 10.4; Br, 15.4%.

And starting material (200 mg, 22%)

2-[(2-Chloroethyl)-3-({[3-(4-morpholinyl)propyl]amino}carbonyl)-2,4-dinitroanilino]ethyl methanesulfonate (IIc9).

Reaction of the acid chloride from 17 (1.3 g) in Me$_2$CO with 3-(4-morpholinyl)propylamine (1.0 mL) at 0° C. as described above, followed by chromatography of the product on silica gel and elution with EtOAc/MeOH (9:1 to 4:1), gave IIc9 (0.37 g, 25%):

mp (EtOAc/petroleum ether) 113-116° C.; $^1$H NMR [(CD$_3$)$_2$SO] δ 8.79 (t, J=5.6 Hz, 1H, CONH), 8.25 (d, J=9.4 Hz, 1H, H-5), 7.65 (d, J=9.4 Hz, 1H, H-6), 4.28 (t, J=5.3, 2H), 3.73 (t, J=6.3, 2H), 3.66 (t, J=5.2, 2H), 3.60 (t, J=5.9, 2H), 3.56 (m, 4H), 3.17 (m, 5H), 2.34 (m, 6H), 1.61 (m, 2H); $^{13}$C NMR δ 161.07, 146.44, 140.44, 137.62, 129.23, 127.60, 122.92, 66.81, 66.12, 55.40, 53.19, 52.85, 50.10, 41.45, 37.30, 36.56, 25.12. HRMS m/z (M+1)$^+$ requires C$_{19}$H$_{29}$$^{35}$ClN$_5$O$_9$S: 538.13745. Found: 538.13869.

Later eluates gave 2-[{2-[(methylsulfonyl)oxy]ethyl}-3-({[3-(4-morpholinyl)propyl]amino}carbonyl)-2,4-dinitroanilino]ethyl methanesulfonate (18f) (0.93 g, 56%) as a yellow solid, mp (EtOAc/petroleum ether) 90-95° C.; $^1$H NMR [(CD$_3$)$_2$SO] δ 8.79 (t, J=5.7 Hz, 1H, CONH), 8.25 (d, J=9.4 Hz, 1H, H-5), 7.65 (d, J=9.4 Hz, 1H, H-6), 4.28 (t, J=5.3, 4H), 3.64 (t, J=5.2, 4H), 3.55 (t, J=4.6, 4H), 3.15 (m, 8H), 2.34 (m, 6H), 1.61 (m, 2H); $^{13}$C NMR δ 161.03, 146.55, 140.90, 137.97, 129.10, 127.56, 123.43, 66.72, 66.12, 55.39, 53.19, 50.37, 37.29, 36.55, 25.13. HRMS m/z (M+1)$^+$ requires C$_{20}$H$_{32}$N$_5$O$_{12}$S$_2$: 598.14889. Found: 598.14894.

2-[(2-Bromoethyl)-3-({[3-(4-morpholinyl)propyl]amino}carbonyl)-2,4-dinitroanilino]ethyl methanesulfonate (IIc10).

LiBr (107 mg, 1.3 mmol) was added in one portion to a warm solution of 18f (0.53 g, 0.89 mmol) in EtOAc (50 mL). The reaction mixture was heated to 60° C. for 2 h, then volatiles were removed under reduced pressure, and the residue was adsorbed directly onto silica gel and chromatographed. Elution with EtOAc/MeOH (10:1 to 5:1) gave 3-[bis(2-bromoethyl)amino]-N-[3-(4-morpholinyl)propyl]-2,6-dinitrobenzamide (19f) (109 mg, 22%) as a foam;

$^1$H NMR [(CD$_3$)$_2$SO] δ 8.77 (t, J=5.6 Hz, 1H, CONH), 8.23 (d, J=9.4 Hz, 1H, H-5), 7.63 (d, J=9.4 Hz, 1H, H-6), 3.68 (m, 4H), 3.57 (m, 8H), 3.17 (m, 2H), 2.34 (m, 6H), 1.61 (m, 2H). HRMS: C$_{15}$H$_{11}$$^{79}$Br$_2$N$_4$O$_5$ requires m/z 438.9253. Found: 438.9228.

Later eluates gave IIc10 (293 mg, 57%):

mp (EtOAc/petroleum ether) 114-117° C.; $^1$H NMR [(CD$_3$)$_2$SO] δ 8.79 (t, J=5.6 Hz, 1H, CONH), 8.25 (d, J=9.4 Hz, 1H, H-5), 7.65 (d, J=9.4 Hz, 1H, H-6), 4.28 (t, J=5.2, 2H), 3.66 (m, J=5.2, 4H), 3.56 (m, J=4.6, 6H), 3.17 (m, 5H), 2.34 (m, 6H), 1.61 (m, 2H); $^{13}$C NMR δ 161.07, 146.22, 140.39, 137.65, 129.21, 127.62, 122.92, 66.83, 66.07, 55.37, 53.15, 52.83, 49.99, 37.28, 36.57, 29.97, 25.07. HRMS m/z (M+1)$^+$ requires C$_{19}$H$_{29}$$^{79}$BrN$_5$O$_9$S: 582.08694. Found: 582.08639.

Later eluates gave starting material 18f (124 mg, 23%).

The following Tables 2 and 3 give biological data for the compounds listed in Table 1.

TABLE 2

Relative cytotoxicities of selected examples of the compounds of Table 1 in NTR-transfected cell lines (18 h exposure).

| | Human Ovarian[a] | | | Human colon[b] | | |
|---|---|---|---|---|---|---|
| | IC$_{50}$[d] | | | IC$_{50}$[d] | | |
| No | NR− | NR+ | Ratio[e] | NR− | NR+ | Ratio[e] |
| Examples of formula IIa | | | | | | |
| IIa2 | 226 | 0.84 | 280 | 150 | 0.69 | 235 |
| IIa3 | 135 | 0.19 | 715 | 80 | 0.22 | 387 |
| IIa4 | 97 | 0.33 | 311 | 70 | 0.41 | 172 |
| IIa5 | 286 | 0.61 | 470 | 192 | 0.77 | 250 |
| IIa6 | | | | 453 | 5.0 | 91 |
| IIa7 | 1110 | 1.74 | | 804 | 3.0 | 268 |
| Examples of formula IIb | | | | | | |
| IIb1 | 80 | 0.04 | 1890 | 20 | 0.07 | 303 |
| IIb2 | 6.0 | 0.007 | 762 | 4.3 | 0.02 | 227 |
| IIb3 | 5.2 | 0.04 | 142 | 3.7 | 0.06 | 66 |
| IIb4 | | | | 9[f] | 0.29[f] | 31[f] |
| IIb5 | | | | 2.9[f] | 0.25[f] | 12[f] |
| IIb6 | 26 | 0.19 | 140 | 11 | 0.21 | 52 |
| IIb7 | 3.1 | 0.03 | 102 | 0.89 | 0.05 | 22 |
| IIb8 | 9.7 | 0.19 | 51 | 4.3 | 0.36 | 13 |
| IIb9 | 3.7 | 0.15 | 25 | 1.44 | 0.24 | 6.3 |
| Examples of formula IIc | | | | | | |
| IIc1 | 196 | 0.55 | 390 | 121 | 1.0 | 120 |
| IIc2 | 150 | 0.21 | 724 | 85 | 0.31 | 271 |
| IIc3 | | | | 425[f] | 5.1[f] | 83[f] |
| IIc4 | 800 | 1.6 | 549 | 392 | 2.6 | 215 |
| IIc5 | 280 | 0.57 | 497 | 209 | 0.85 | 301 |
| IIc6 | | | | 314[f] | 20[f] | 16[f] |
| IIc7 | 1680 | 6.6 | 267 | 856 | 4.3 | 262 |
| IIc8 | 890 | 1.8 | 509 | 214 | 1.5 | 141 |
| IIc9 | 433 | 32 | 14 | 262 | 31 | 8.3 |
| IIc10 | 156 | 11 | 14 | 94 | 11 | 8.2 |

Footnotes for Table 2
[a]Human ovarian: wild-type (NR−) is SKOV3, transfected (NR+) is SC3.2.
[b]Human colon: wild-type (NR−) is WIDR, transfected (NR+) is WC14.10.
[c]Chinese hamster fibroblast: wild-type (NR−) is T-78-1, transfected (NR+) is T79-A3.
[d]IC$_{50}$: the concentration of drug (in micromolar) required to reduce cell numbers to 50% of controls at the end of the evaluation period.
[e]Ratio = IC$_{50}$(NR−)/IC$_{50}$(NR+).
[f]4 h exposure.

TABLE 3

Relative cytotoxicities of selected examples of the compounds of Table 1 in oxic and anoxic tumour cells.

| | IC$_{50}$s in A549 human lung carcinoma cells (4 h exposure) in μM[a] | | | |
|---|---|---|---|---|
| No | WT[b] anoxic | WT Ratio[c] | P450R[d] anoxic | P450R ratio[c] |
| Examples of formula IIa | | | | |
| IIa5 | 139 | 5.2 | 73 | 9.9 |
| IIa6 | 348 | 2.4 | 31 | 18 |
| Examples of formula IIb | | | | |
| IIb3 | 2.3 | 26 | 0.28 | 133 |
| IIb4 | 4.5 | 7 | 0.45 | 95 |
| IIb5 | 4 | 19 | 0.34 | 150 |

TABLE 3-continued

Relative cytotoxicities of selected examples of the compounds of Table 1 in oxic and anoxic tumour cells.

| | IC$_{50}$s in A549 human lung carcinoma cells (4 h exposure) in μM[a] | | | |
|---|---|---|---|---|
| No | WT[b] anoxic | WT Ratio[c] | P450R[d] anoxic | P450R ratio[c] |
| Examples of formula IIc | | | | |
| IIc3 | 28 | 20 | 2.9 | 146 |
| IIc4 | 82 | 26 | 7.3 | 108 |
| IIc5 | 52 | 30 | 4.5 | 134 |

Footnotes for Table 3.
[a]Human lung carcinoma line.
[b]Wild-type.
[c]Ratio = IC$_{50}$(aerobic)/IC$_{50}$(anoxic).
[d]A549 transfected with human cytochrome P450 reductase (P450R).

It is clear from the data of Tables 2 and 3 that the examples of the nitroaniline derivatives of the invention include compounds which are active as cytotoxic agents, and which have the additional capability of being reductively activated by the *E. coli* NTR and/or by endogenous reductase enzymes under hypoxia.

Wherein the foregoing description reference has been made to reagents, or integers having known equivalents thereof, then those equivalents are herein incorporated as if individually set forth.

While this invention has been described with reference to certain embodiments and examples, it is to be appreciated that further modifications and variations may be made to embodiments and examples provided without departing from the scope of the invention.

We claim:

1. 2((2-Bromoethyl)-2-{[(2-hydroxyethyl)amino]carbonyl}-4,6-dinitroanilino)ethyl methanesulfonate.

2. A nitroaniline-based unsymmetrical mustard represented by formula (IIIb)

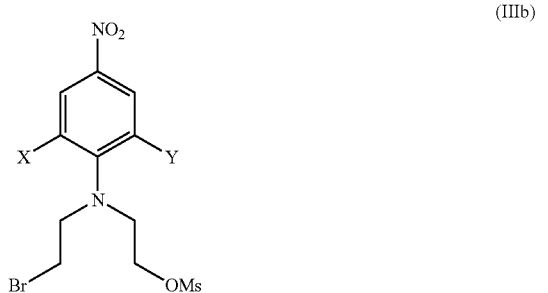

(IIIb)

wherein

X represents one of the groups $NO_2$, CN, or $SO_2R^1$, where $R^1$ represents a $C_{1-6}$-alkyl optionally substituted with one or more hydroxy and/or one or more amino groups;

Y represents one of the groups $OR^2$, $NHCOR^2$, $CONHR^2CO_2R^3$, $CONHR^2$-morpholide, $CONHR^2$ other than $CONH_2$, $CONR^2R^3$ other than $CONH_2$, $CONHOR^2$, $CONHSO_2R^2$, $SO_2NH_2$, $SO_2NHR^2$ or $SO_2NR^2R^3$ wherein each $R^2$ and $R^3$ independently represent a H, $C_{1-6}$-alkyl or $C_{1-6}$-alkylene optionally substituted with one or more hydroxy and/or one or more amino groups; and A and B each independently represent halogen, $OSO_2R^4$, $OSO_2NH_2$, $OSO_2NHR^4$ or $OSO_2NR^4R^5$, wherein each $R^4$ and $R^5$ independently represent a $C_{1-6}$-alkyl optionally substituted with one or more hydroxy and/or one or more amino groups; and pharmaceutically acceptable derivatives and salts thereof.

3. A method of preparing a nitroaniline-based unsymmetrical mustard represented by formula (IIIb) as claimed in claim 2

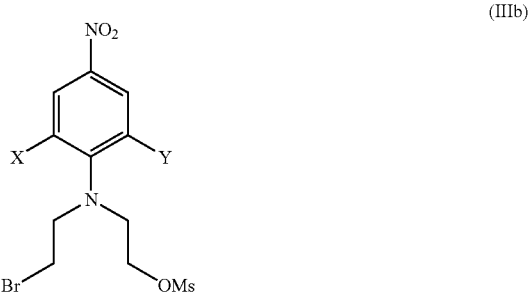

(IIIb)

wherein

X represents one of the groups $NO_2$, CN, or $SO_2R^1$, where $R^1$ represents a $C_{1-6}$-alkyl optionally substituted with one or more hydroxy and/or one or more amino groups;

Y represents one of the groups $OR^2$, $NHCOR^2$, $CONHR^2CO_2R^3$, $CONHR^2$-morpholide, $CONHR^2$ other than $CONH_2$, $CONR^2R^3$ other than $CONH_2$, $CONHOR^2$, $CONHSO_2R^2$, $SO_2NH_2$, $SO_2NHR^2$ or $SO_2NR^2R^3$ wherein each $R^2$ and $R^3$ independently represent a H, $C_{1-6}$-alkyl or $C_{1-6}$-alkylene optionally substituted with one or more hydroxy and/or one or more amino groups; and A and B each independently represent halogen, $OSO_2R^4$, $OSO_2NH_2$, $OSO_2NHR^4$ or $OSO_2NR^4R^5$, wherein each $R^4$ and $R^5$ independently represent a $C_{1-6}$-alkyl optionally substituted with one or more hydroxy and/or one or more amino groups; and pharmaceutically acceptable derivatives and salts thereof;

the method comprising the step of reacting a compound of formula

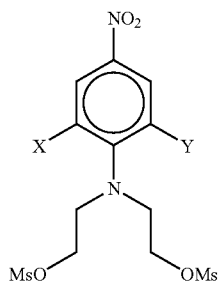

with an amount of LiBr in a polar solvent to give a bromo mesylate of formula (IIIb).

4. The method as claimed in claim 3 wherein the polar solvent is selected from the group consisting of acetonitrile, dimethylformamide, ethyl acetate, triethylamine, acetone and mixtures thereof.

5. The method as claimed in claim 3 wherein the alkali metal halide is selected from the group consisting of LiCl, LiBr, NaI and NaBr.

6. A compound of formula (IIIb) obtained by any one of the methods as claimed in claim 3.

7. A method of cell ablation therapy utilising at least one endogenous nitroreductase enzyme, the method comprising the step of administering a compound of Formula (IIIb) as claimed in claim 2 in a "therapeutically effective amount" to ablate tumour cells in tissue in a subject, wherein said tumor cells have regions of hypoxia and express at least one endogenous nitroreductase enzyme, to activate the compound of formula (IIIb) into an active metabolite to ablate the tumor cells.

8. A pharmaceutical composition comprising a therapeutically effective amount of a compound of formula (IIIb) as defined in claim 2 and a pharmaceutically acceptable excipient, adjuvant, carrier, buffer or stabiliser.

9. A nitroaniline-based unsymmetrical mustard as claimed in claim 2, wherein Y is $CONHR_2$ where $R_2$ is $C_1$-$C_6$ alkylene substituted with hydroxyl.

10. A nitroaniline-based unsymmetrical mustard as claimed in claim 2, wherein Y is $CONHCH_2CH_2OH$.

* * * * *